US009868769B2

(12) United States Patent
Bearson et al.

(10) Patent No.: US 9,868,769 B2
(45) Date of Patent: Jan. 16, 2018

(54) MUTATED *SALMONELLA ENTERIACA*

(71) Applicant: THE UNITED STATES OF AMERICA, AS REPRESENTED BY THE SECRETARY OF AGRICULTURE, Washington, DC (US)

(72) Inventors: Bradley L. Bearson, Ames, IA (US); Shawn M. Bearson, Ames, IA (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 15/108,725

(22) PCT Filed: Dec. 29, 2014

(86) PCT No.: PCT/US2014/072486
§ 371 (c)(1),
(2) Date: Jun. 28, 2016

(87) PCT Pub. No.: WO2015/103104
PCT Pub. Date: Jul. 9, 2015

(65) Prior Publication Data

US 2017/0008935 A1 Jan. 12, 2017

Related U.S. Application Data

(60) Provisional application No. 61/923,941, filed on Jan. 6, 2014.

(51) Int. Cl.

| | |
|---|---|
| *A61K 39/112* | (2006.01) |
| *C07K 14/255* | (2006.01) |
| *A61K 39/00* | (2006.01) |

(52) U.S. Cl.
CPC ........ *C07K 14/255* (2013.01); *A61K 39/0275* (2013.01); *A61K 2039/522* (2013.01); *A61K 2039/543* (2013.01); *A61K 2039/55* (2013.01); *A61K 2039/552* (2013.01); *A61K 2039/58* (2013.01)

(58) Field of Classification Search
CPC ........ A61K 2039/522; A61K 2039/543; A61K 2039/55; A61K 2039/552; A61K 2039/58; A61K 39/0275; C07K 14/255
See application file for complete search history.

(56) References Cited

U.S. PATENT DOCUMENTS

2009/0258037 A1 10/2009 Hammond

FOREIGN PATENT DOCUMENTS

| | | | |
|---|---|---|---|
| WO | 0004919 | A2 | 2/2000 |
| WO | 03-096812 | A1 | 11/2003 |
| WO | 03038116 | A2 | 8/2008 |
| WO | 2010084350 | A1 | 7/2010 |
| WO | 2011092185 | A1 | 8/2011 |
| WO | 2012092226 | A1 | 7/2012 |

OTHER PUBLICATIONS

Bearson, Bradley L. et al. "An Attenuated *Salmonella enterica* serovar Typhimurium Strain Reduces Disease Severity, Fecal Shedding, and Gatrointestinal Colonization in Swine following Virulent S. Typhimurium Challenge". In: Abstracts of the 111th General Meeting of the American Society for Microbiology, May 21-24, 2011, New Orleans, Louisana. p. 179.

Bearson, Bradley et al., "A DIVA vaccine for cross-protection agaianst *Salmonella*" (2016), Vaccine 34, 1241-1246.

Bearson, Bradley L., et al. "Iron regulated genes of *Salmonella enterica* serovar Typhimurium in response to norepinephrine and the requirement of fepDGC for norepinephrine-enhanced growth", (2008) Microbes and Infection 10; 807-816.

Bearson, Bradley L., "Serological Response of Swine to an Attenuated *Salmonella enterica* serovar Typhimurium Strain that Reduces Gastrointestinal Colonization, Fecal Shedding and Disease due to Virulent *Salmonella*. Typhimurium". (2011) 9th International Conference on the Epidemiology and Control of biological, chemical and physical hazards in pigs and pork, Maastricht, Netherlands. p. 228.

Park, Yang-Nim et al, "Application of the FLP/FRT system for conditional gene delection in yeast *Saccharomyces cerevisiae*" (2011) Yeast 28: 673-681.

Hebrard, Magali et al., "sRNAs and the virulence of *Salmonella enterica* serovar Typhimurium" (2012) RNA Biology, 9:4, 437-445.

Kint, Gwendoline et al. "The small regulatory RNA molecule MicA is involved in *Salmonella enterica* serovar Typhimurium biofilm formation", (2010) BMC Mircrobiology, 10:276, 1-8.

Kong, Qingke, et al. "Regulated Delayed Expression of rfaH in an Attenuated *Salmonella enterica* Serovar Typhimurium Vaccine Enhances Immunogenicity of Outer Membrane Proteins and a Heterologous Antigen" (2009), American Society for Microbiology, Infection and Immunity, 77(12), 5572-5582.

(Continued)

*Primary Examiner* — S. Devi

(74) *Attorney, Agent, or Firm* — David L. Marks; John D. Fado

(57) ABSTRACT

A novel, mutated *Salmonella enterica* serovar Typhimurium vaccine is generated and imparts protective immunity in vaccinated animals for a range of *S. enterica* serovars. The vaccine can be attenuated or inactivated, including bacterial ghosts or membrane fractions thereof. Immunogenic compositions are included in the invention and methods of generating an immune response.

23 Claims, 16 Drawing Sheets

(56) References Cited

OTHER PUBLICATIONS

Kong, Qingke et al. "Effect of Deletion of Genes Involved in Lipopolysaccharide Core and O-Antigen Synthesis on Virulence and Immunogenicity of *Salmonella enterica* Serovar Typhimurium" (2011), American Society for Microbiology, Infection and immunity, 79(10), 4227-4239.

Leyman, Bregje et al. "*Salmonella* Typhimurium LPS mutations for use in vaccines allowing differentiation of infected and vaccinated pigs", (2011), Vaccine 29, 3679-3685.

Moon, Kyung et al. "A PhoQ/P-regulated small RNA regulates sensitivity of *Escherichia coli* to antimicrobial peptides", (2009), Molecular Microbiology, 74(6), 1314-1330.

Nagy, Gabor, et al. "Oral Immunization with rfaH Mutant elicits Protection against Salmonellosis in Mice", (2004), American Society for Microbiology, Infection and Immunity, 72(7), 4297-4301.

Nagy, Babor, et al. "Down-Regulation of Key Virulence Factors Makes the *Salmonella enterica* Serovar Typhimurium rfaH Mutant a Promising Live-Attenuated Vaccine Candidate", (2006), American Society for Microbiology, Infection and Immunity, 74(10), 5914-5925.

Nagy, Gabor et al. "Gently Rough": The Vaccine Potential of a *Salmonella enterica* Regulatory Lipopolysaccharide Mutant, (2008), JID, 198, (1699-1706).

Papenfort, Kai, et al. "Regulatory RNA in Bacterial Pathogens", Cell Host & Microbe, (2010), Elsevier Inc., 8:116-127.

Papenfort, Kai, et al. "δE-dependent small RNAs of *Salmonella* respond to membrane stress by accelerating global bmp mRNA decay", (2006), Molecular Microbiology, 62(6), 1674-1688.

Santiviago, Carlos A., et al. "Analysis of Pools of Targeted *Salmonella* Deletion Mutants Identifies Novel Genes Affecting Fitness during Competitive Infection in Mice", (2009) PLoS Pathogens, 5(7), e1000477.

Ramachandran, Vinoy K., et al. "The architecture and ppGpp-dependent expression of the primary transcriptome of *Salmonella* Typhimurium during invasion gene expression," BMC Genomics, (2012), 13:25, doi: 10.1-50.

Vogel, Jorg, et al. "Small non-coding RNAs and the bacterial outer membrane" (2006), Science Direct, Current Opinion in Microbiology, 9:605-611.

SEQUENCE LISTING

```
<160> NUMBER OF SEQ ID NOS: 10

<210> SEQ ID NO 1
<211> LENGTH: 67
<212> TYPE: DNA
<213> ORGANISM: Artificial Sequence
<220> FEATURE:
<223> OTHER INFORMATION: Primer; hybrid sequence

<400> SEQUENCE: 1
atgcaatcct ggtatttact gtactgcaaa cgcgggcaac ttcagcatag agcagtgacg    60
tagtcgc                                                              67

<210> SEQ ID NO 2
<211> LENGTH: 67
<212> TYPE: DNA
<213> ORGANISM: Artificial Sequence
<220> FEATURE:
<223> OTHER INFORMATION: Primer; hybrid sequence

<400> SEQUENCE: 2
ctaaatcttg cgaaaaccgg tgttttttac gctctgcttc acttcgatag ctgaatgagt    60
gacgtgc                                                              67
```

```
<210> SEQ ID NO 3
<211> LENGTH: 63
<212> TYPE: DNA
<213> ORGANISM: Artificial Sequence
<220> FEATURE:
<223> OTHER INFORMATION: Primer; hybrid sequence

<400> SEQUENCE: 3
ctgaagtttg cctttaagtg aaaaaatttt gccaataggt cgatagctga atgagtgacg      60
tgc                                                                   63

<210> SEQ ID NO 4
<211> LENGTH: 66
<212> TYPE: DNA
<213> ORGANISM: Artificial Sequence
<220> FEATURE:
<223> OTHER INFORMATION: Primer; hybrid sequence

<400> SEQUENCE: 4
caaaaaaccc accaaccttg aaccgaaatg gcggggttga tgggcataga gcagtgacgt      60
agtcgc                                                                66

<210> SEQ ID NO 5
<211> LENGTH: 65
<212> TYPE: DNA
<213> ORGANISM: Artificial Sequence
<220> FEATURE:
<223> OTHER INFORMATION: Primer; hybrid sequence

<400> SEQUENCE: 5
gattacacga gttgcgtaac aggagcgata gcaaaatagg ttcgatagct gaatgagtga      60
cgtgc                                                                 65

<210> SEQ ID NO 6
<211> LENGTH: 66
<212> TYPE: DNA
<213> ORGANISM: Artificial Sequence
<220> FEATURE:
<223> OTHER INFORMATION: Primer; hybrid sequence

<400> SEQUENCE: 6
caaatctttc gttacagttt gcgaagcgct gttgcgattg tctgcataga gcagtgacgt      60
agtcgc                                                                66

<210> SEQ ID NO 7
<211> LENGTH: 64
<212> TYPE: DNA
<213> ORGANISM: Artificial Sequence
<220> FEATURE:
<223> OTHER INFORMATION: Primer; hybrid sequence

<400> SEQUENCE: 7
ctgaactctt tgttccgggg cgagtctgag tatatgaaag acgatagctg aatgagtgac      60
gtgc                                                                  64

<210> SEQ ID NO 8
<211> LENGTH: 60
<212> TYPE: DNA
<213> ORGANISM: Artificial Sequence
<220> FEATURE:
<223> OTHER INFORMATION: Primer; hybrid sequence

<400> SEQUENCE: 8
```

```
cgtggcttgc aaaacacgcc tgacccaaaa gaaaaaggca tagagcagtg acgtagtcgc        60

<210> SEQ ID NO 9
<211> LENGTH: 67
<212> TYPE: DNA
<213> ORGANISM: Artificial Sequence
<220> FEATURE:
<223> OTHER INFORMATION: Primer; hybrid sequence

<400> SEQUENCE: 9
ctgaactcat catgatataa ttaagaccat attttgcatt gccacgatag ctgaatgagt        60
gacgtgc                                                                 67

<210> SEQ ID NO 10
<211> LENGTH: 62
<212> TYPE: DNA
<213> ORGANISM: Artificial Sequence
<220> FEATURE:
<223> OTHER INFORMATION: Primer; hybrid sequence

<400> SEQUENCE: 10
ccaagtctgg gaggccgttc tttatcacaa ataaaaaaag catagagcag tgacgtagtc        60
gc                                                                      62
```

MUTATED *SALMONELLA ENTERIACA*

CROSS-REFERENCE TO RELATED APPLICATIONS

This is a National Phase Application filed under 35 U.S.C. 371 as a national stage of PCT/US2014/072486, filed Dec. 29, 2014, and this application claims priority to U.S. Patent Application 61/923,941 filed Jan. 6, 2014, the content of each of which is hereby incorporated by reference in its entirety.

The Sequence Listing submitted in text format (.txt) filed on Jun. 28, 2016, named "0068.12SequenceListing.txt", (created on Dec. 9, 2014, 3 KB), is incorporated herein by reference.

BACKGROUND OF THE INVENTION

Field of Invention

This invention relates to a novel, mutated *Salmonella enterica* serovar Typhimurium that can be used to generate an immune response in porcine and avian, in particular, and in other animals, in general. This immune response helps reduce morbidity and mortality caused by any serovar of *Salmonella enterica* and reduces transmission, colonization and carriage of any serovar of *Salmonella enterica* in the animal.

Description of the Prior Art

Bacteria of the genus *Salmonella* spp. are notorious for their pathogenicity in both man and animal. There are greater than 2,400 *Salmonella* serovars that are ubiquitous in the environment and can colonize food producing animals and poultry as well as wild animals and birds without causing overt disease. In the U.S. alone, on a yearly basis the number of humans suffering from *Salmonella* infections exceeds one million cases. In most cases, the infection is caused by contaminated food. Well-known sources of infection are eggs (from both ducks and chickens), products containing eggs, and insufficiently heated poultry, bovine, and porcine meat. The ability to cope with such infections is low, especially in infants, young children, elderly people and immune compromised people. In these groups, the yearly death rate caused by *Salmonella* infections is high. During the last few decades large-scale animal husbandry has led to an enormous increase in animal density. As a result, an increase is seen in the number of animal infections and, subsequently, in the number of human infections caused by contaminated food. It is clear that animals are the main source of *Salmonella* infection in humans. This source is very difficult to control for the following reasons. First, *Salmonella* infections usually cause no serious illness in healthy, full-grown animals; these animals can carry the bacterium for a prolonged period. Carrier animals shed the bacterium in their feces. Thus it is practically impossible for young animals to avoid infection. Second, many *Salmonella* species colonize several different host species. Some *Salmonella* species cause primary infections in specific hosts; other *Salmonella* species are not restrictive at all. As primary infectans, *S. enterica* serovar Typhi and *S. enterica* serovar Paratyphi are frequently associated with infection in man whereas *S. enterica* serovar Dublin is a causative agent of disease in cattle. *S. enterica* serovar Abortus-equi causes abortion in horses; *S. enterica* serovar Abortus-ovi causes abortion in sheep. *S. enterica* serovar Choleraesuis is the cause of lethal diarrhea in young pigs; *S. enterica* serovar Typhimurium and *S. enterica* serovar Enteritidis cause salmonellosis in humans, poultry, pigs, cattle and rodents. *S. enterica* serovar Arizonae causes disease in turkeys, whereas *S. enterica* serovar Gallinarum causes salmonellosis only in poultry.

Several years ago, greater than 50% of swine production sites (representing 94% of the U.S. swine inventory) tested positive for *Salmonella* spp. Swine that are *Salmonella* carriers are a food safety risk for consumers of pork, an animal health risk to non-colonized/uninfected pigs, and an environmental risk caused by fecal shedding of the pathogen into manure that is used as a soil amendment. Also several years ago, approximately 40% of U.S. dairy operations tested positive for *Salmonella* spp., and approximately 28% of dairy operations tested positive for *Salmonella* in either bulk tank milk or in-line milk filters by RT-PCR. Further, in a more recent study, approximately 9% of beef cow-calf operations were positive for *Salmonella* spp.

Clearly there is a need for safe and efficacious vaccines to combat the various *Salmonella* species not only to prevent disease in animals but also to reduce subclinical infections in food-producing animals that are a source of foodborne disease in humans. Although attenuated *Salmonella* vaccines are currently available for swine, these vaccines tend to be *Salmonella* serovar specific and, therefore, do not provide broad protection against many *Salmonella* serovars. For example, Boehringer Ingelheim Vetmedica sells an avirulent, attenutated *S. enterica* serovar Choleraesuis vaccine called Enterisol® SC-54 that provides good protection against *S. enterica* serovar Choleraesuis infections in swine but does not protect against other *Salmonella* species. Lohmann Animal Health sells AviPro® MEGAN®VAC 1, an attenuated *S. enterica* serovar Typhimurium that slightly reduces the amount of *S. enterica* serovar Typhimurium, *S. enterica* serovar Enteritidis and *S. enterica* serovar Heidelberg in the organs of young growing chickens and *S. enterica* serovar Enteritidis colonization of the crop and digestive tract, including the ceca. However, one can improve greatly upon the efficacy of both of these vaccines.

Prior art approaches to generate attenuated *Salmonella* spp. used a limited set of mutations. See, e.g., Cardenas, et al., *Clin. Microbial Rev.* 5:328-342 (1992); Chatfield, et al., *Vaccine* 7:495-498 (1989). These approaches include (i) temperature sensitive mutants (Fahey, et al., *Infect. Immun.* 1:263-270 (1970)), (ii) mutants defective for aroA, asd, cys, or thy (Galan, et al., *Gene* 94:29-35 (1990); Hoiseth, et al., *Nature* 291:238-239 (1981); Robertsson, et al., *Infect. Immun.* 41:742-750 (1983)), (iii) Δpur and Δdap mutants (Clarke, et al., *J. Vet. Res.* 51:32-38 (1987); McFarland, et al., *Microb. Pathog.* 3:129-141 (1987)), (iv) strains defective in carbohydrate metabolism (e.g. ΔgalE (Germanier, et al., *Infect. Immun.* 4:663-673 (1971); Hone, et al., *J. Infect. Dis.* 156:167-174 (1987)), (v) lipopolysaccharide synthesis defective strains (e.g., galE, pmi, rfa) (e.g., Nagy, et al., *Infect. Immun.* 74(10):5914-5925 (2006) and Nagy, et al., *Infect. Immun.* 72(7):4297-4301 (2004)), and (vi) strains lacking plasmids and mutants lacking virulence genes (e.g., invA). However, the effectiveness of these approaches is doubtful because, at least until now, they have been unable to confer long term immunity against *Salmonella* infections and have not been effective against a broad range of *Salmonella* spp.

There remains a need for a mutated *Salmonella* immunogenic composition capable of inducing high immune responses in animals. It is expected that such a mutated *Salmonella* immunogenic composition would induce a strong immune response in an animal, be cross-protective against other *Salmonella* species (or at least other serovars), and reduce colonization and fecal shedding of *Salmonella* species. Further such a mutated *Salmonella* immunogenic composition would be attenuated compared to the wild-type *Salmonella* bacteria. Such an immunogenic composition would limit the colonization of swine and other animals with *Salmonella* spp. (or at least other serovars), thereby reducing pathogen transmission and the risks to public health, animal health, and the environment. This invention involves a *S. enterica* serovar Typhimurium containing one or more mutations in rfaH, omrA, omrB, rybB, micA, and/or invR and the use of the mutated *S. enterica* serovar Typhimurium to generate in animals an immune response cross-reactive to other *Salmonella enterica* serovars.

BRIEF DESCRIPTION OF THE INVENTION

It is an object of this invention to have a novel, mutated *Salmonella enterica* serovar Typhimurium having at least one mutation in at least one gene involved in LPS synthesis and at least one mutation in at least one sRNA gene selected from the group consisting of rybB, micA, omrA, omrB, and invR.

It is an object of this invention to have a novel, mutated *S. enterica* serovar Typhimurium having at least one mutation in at least one gene involved in LPS synthesis and at least one mutation in at least one sRNA gene selected from the group consisting of rybB, micA, omrA, omrB, and invR. It is a further object of this invention that the at least one mutation in at least one sRNA gene is a null mutation in omrA and omrB. It is another object of this invention that this novel, mutated *S. enterica* serovar Typhimurium is a live attenuated bacteria or an inactivated bacteria. In one embodiment of this invention, the novel, mutated *S. enterica* serovar Typhimurium is a bacterial ghost or membrane fractions of the *S. enterica* serovar Typhimurium.

It is an object of this invention to have a novel, mutated *S. enterica* serovar Typhimurium having at least one null mutation in each of rfaH, omrA, and omrB. It is another object of this invention that this novel, mutated *S. enterica* serovar Typhimurium is a live attenuated bacteria or an inactivated bacteria. In one embodiment of this invention, the novel, mutated *S. enterica* serovar Typhimurium is a bacterial ghost or membrane fractions of the *S. enterica* serovar Typhimurium.

It is an object of this invention to have a novel, mutated *S. enterica* serovar Typhimurium having at least one null mutation in each of rfaH, rybB, micA, omrA, omrB, and invR. It is another object of this invention that this novel, mutated *S. enterica* serovar Typhimurium is a live attenuated bacteria or an inactivated bacteria. In one embodiment of this invention, the novel, mutated *S. enterica* serovar Typhimurium is a bacterial ghost or membrane fractions of the *S. enterica* serovar Typhimurium. In another embodiment, the *S. enterica* serovar Typhimurium is strain BBS 866 which is Patent Deposit Accession Number NRRL B-50989. In another embodiment, the *S. enterica* serovar Typhimurium is strain BBS 1134 which is Patent Deposit Accession Number NRRL B-50990.

It is an object of this invention to have an immunogenic composition that contains a novel, mutated *S. enterica* serovar Typhimurium having at least one mutation in at least one gene involved in LPS synthesis and at least one mutation in at least one sRNA gene selected from the group consisting of rybB, micA, omrA, omrB, and invR; and a pharmaceutically acceptable carrier or diluent. It is another object of this invention that this novel, mutated *S. enterica* serovar Typhimurium is a live attenuated bacteria or an inactivated bacteria. In one embodiment of this invention, the novel, mutated *S. enterica* serovar Typhimurium is a bacterial ghost or membrane fractions of the *S. enterica* serovar Typhimurium. It is an optional embodiment that the immunogenic composition contains an adjuvant.

It is an object of this invention to have an immunogenic composition that contains a novel, mutated *S. enterica* serovar Typhimurium having at least a null mutation in rfaH, omrA, and omrB; and a pharmaceutically acceptable carrier or diluent. It is another object of this invention that this novel, mutated *S. enterica* serovar Typhimurium is a live attenuated bacteria or an inactivated bacteria. In one embodiment of this invention, the novel, mutated *S. enterica* serovar Typhimurium is a bacterial ghost or membrane fractions of the *S. enterica* serovar Typhimurium. It is an optional embodiment that the immunogenic composition contains an adjuvant.

It is an object of this invention to have an immunogenic composition that contains a novel, mutated *S. enterica* serovar Typhimurium having at least a null mutation in each of rfaH, rybB, micA, omrA, omrB, and invR; and an immunologically acceptable carrier or diluent. It is another object of this invention that this novel, mutated *S. enterica* serovar Typhimurium is a live attenuated bacteria or an inactivated bacteria. In one embodiment of this invention, the novel, mutated *S. enterica* serovar Typhimurium is a bacterial ghost or membrane fractions of the *S. enterica* serovar Typhimurium. It is an optional embodiment that the immunogenic composition contains an adjuvant. In another embodiment, the *S. enterica* serovar Typhimurium is strain BBS 866 which is Patent Deposit Accession Number NRRL B-50989. In another embodiment, the *S. enterica* serovar Typhimurium is strain BBS 1134 which is Patent Deposit Accession Number NRRL B-50990.

It is an object of this invention to have a method for inducing an immune response in an animal to *S. enterica* by administering to the animal an immunologically effective amount of a novel, mutated *S. enterica* serovar Typhimurium having at least one mutation in at least one gene involved in LPS synthesis and at least one mutation in at least one sRNA gene selected from the group consisting of rybB, micA, omrA, omrB, and invR or by administering an immunogenic composition containing this novel, mutated *S. enterica* serovar Typhimurium. It is another object of this invention to optionally administer an adjuvant with the novel, mutated *S. enterica* serovar Typhimurium or the immunogenic composition containing this novel, mutated *S. enterica* serovar Typhimurium. It is another object of this invention that this novel, mutated *S. enterica* serovar Typhimurium is a live attenuated bacteria or an inactivated bacteria. In one embodiment of this invention, the novel, mutated *S. enterica* serovar Typhimurium is a bacterial ghost or membrane fractions of the *S. enterica* serovar Typhimurium.

It is another object of this invention to have a method for inducing an immune response in an animal to *S. enterica* by administering to the animal an immunologically effective amount of a novel, mutated *S. enterica* serovar Typhimurium having at least one null mutation in each of rfaH, omrA and omrB or by administering an immunogenic composition containing this novel, mutated *S. enterica* serovar Typhimurium. It is another object of this invention that this novel, mutated *S. enterica* serovar Typhimurium is a live attenuated bacteria or an inactivated bacteria. In one embodiment of this invention, the novel, mutated *S. enterica* serovar Typhimurium is a bacterial ghost or membrane fractions of the *S. enterica* serovar Typhimurium. It is another object of this invention to optionally administer an adjuvant with the novel, mutated *S. enterica* serovar Typhimurium or with the immunogenic composition containing this novel, mutated *S. enterica* serovar Typhimurium.

It is another object of this invention to have a method for inducing an immune response in an animal to *S. enterica* by administering to the animal an immunologically effective amount of a novel, mutated *S. enterica* serovar Typhimurium having at least one null mutation in each of rfaH, rybB, micA, omrA, omrB, and invR or by administering an immunogenic composition containing this novel, mutated *S. enterica* serovar Typhimurium. It is another object of this invention that this novel, mutated *S. enterica* serovar Typhimurium is a live attenuated bacteria or an inactivated bacteria. In one embodiment of this invention, the novel, mutated *S. enterica* serovar Typhimurium is a bacterial ghost or membrane fractions of the *S. enterica* serovar Typhimurium. It is another object of this invention to optionally administer an adjuvant with the novel, mutated *S. enterica* serovar Typhimurium or with an immunogenic composition containing this novel, mutated *S. enterica* serovar Typhimurium. In another embodiment, the *S. enterica* serovar Typhimurium is strain BBS 866 which is Patent Deposit Accession Number NRRL B-50989. In another embodiment, the *S. enterica* serovar Typhimurium is strain BBS 1134 which is Patent Deposit Accession Number NRRL B-50990.

It is an object of this invention to have a method for preventing or treating a disease caused by *S. enterica* in an animal by administering to the animal an immunologically effective amount of a novel, mutated *S. enterica* serovar Typhimurium, or of an immunogenic composition which contains this novel, mutated *S. enterica* serovar Typhimurium, and a pharmaceutically acceptable carrier or diluent. It is a further object of this invention that the novel, mutated *S. enterica* serovar Typhimurium has at least one mutation in at least one gene involved in LPS synthesis and at least one mutation in at least one sRNA gene selected from the group consisting of rybB, micA, omrA, omrB, and invR. It is another object of this invention that the immunogenic composition optionally contains an adjuvant or that one administers an adjuvant with this novel, mutated *S. enterica* serovar Typhimurium.

It is an object of this invention to have a method for preventing or treating a disease caused by *S. enterica* in an animal by administering to the animal an immunologically effective amount of a novel, mutated *S. enterica* serovar Typhimurium, or of an immunogenic composition which contains this novel, mutated *S. enterica* serovar Typhimurium, and a pharmaceutically acceptable carrier or diluent. In some embodiments of this invention, the novel, mutated *S. enterica* serovar Typhimurium has a null mutation in rfaH, omrA, and omrB. In other embodiments, the novel, mutated *S. enterica* serovar Typhimurium has a null mutation in each of rfaH, rybB, micA, omrA, omrB, and invR. It is another object of this invention that this novel, mutated *S. enterica* serovar Typhimurium is a live attenuated bacteria or an inactivated bacteria. In one embodiment of this invention, the novel, mutated *S. enterica* serovar Typhimurium is a bacterial ghost or membrane fractions of the *S. enterica* serovar Typhimurium. In another embodiment, the *S. enterica* serovar Typhimurium is strain BBS 866 which is Patent Deposit Accession Number NRRL B-50989. In another embodiment, the *S. enterica* serovar Typhimurium is strain BBS 1134 which is Patent Deposit Accession Number NRRL B-50990. It is another object of this invention that the immunogenic composition optionally contains an adjuvant or that one administers an adjuvant with this novel, mutated *S. enterica* serovar Typhimurium.

It is an object of this invention to have a method for reducing an animal's carriage of *S. enterica* by administering to the animal an immunologically effective amount of a novel, mutated *S. enterica* serovar Typhimurium, a bacterial ghost of this novel, mutated *S. enterica* serovar Typhimurium, or a membrane fraction of this novel, mutated *S. enterica* serovar Typhimurium, or an immunogenic composition containing a pharmaceutically acceptable carrier and this novel, mutated *S. enterica* serovar Typhimurium, a bacterial ghost thereof, and/or membrane fractions thereof. It is a further object of this invention that the novel, mutated *S. enterica* serovar Typhimurium has at least one mutation in at least one gene involved in LPS synthesis and at least one mutation in at least one sRNA gene selected from the group consisting of rybB, micA, omrA, omrB, and invR. It is another object of this invention of optionally administering an adjuvant to the animal. It is another object of this invention that this novel, mutated *S. enterica* serovar Typhimurium is a live attenuated bacteria or an inactivated bacteria. In other embodiments, the novel, mutated *S. enterica* serovar Typhimurium has at least one null mutation in each of rfaH, rybB, micA, omrA, omrB, and invR. In another embodiment, the *S. enterica* serovar Typhimurium is strain BBS 866 which is Patent Deposit Accession Number NRRL B-50989. In another embodiment, the *S. enterica* serovar Typhimurium is strain BBS 1134 which is Patent Deposit Accession Number NRRL B-50990.

It is an object of this invention to have a method for preventing *S. enterica* colonization in an animal by administering to the animal an immunologically effective amount of a novel, mutated *S. enterica* serovar Typhimurium, a bacterial ghost of this novel, mutated *S. enterica* serovar Typhimurium, or a membrane fraction of this novel, mutated *S. enterica* serovar Typhimurium; or of an immunogenic composition which contains this novel, mutated *S. enterica* serovar Typhimurium, a bacterial ghost of thereof, or a membrane fraction thereof; and a pharmaceutically acceptable carrier or diluent. It is a further object of this invention that the novel, mutated *S. enterica* serovar Typhimurium has at least one mutation in at least one gene involved in LPS synthesis and at least one mutation in at least one sRNA gene selected from the group consisting of rybB, micA, omrA, omrB, and invR. In some embodiments of this invention, the novel, mutated *S. enterica* serovar Typhimurium has at least one null mutation in each of rfaH, omrA, or omrB. In other embodiments, the novel, mutated *S. enterica* serovar Typhimurium has at least one null mutation in each of rfaH, rybB, micA, omrA, omrB, and invR. In another embodiment, the *S. enterica* serovar Typhimurium is strain BBS 866 which is Patent Deposit Accession Number NRRL B-50989. In another embodiment, the *S. enterica* serovar Typhimurium is strain BBS 1134 which is Patent Deposit Accession Number NRRL B-50990. It is another object of this invention that the immunogenic composition optionally contains an adjuvant or that one administers an adjuvant with this novel, mutated *S. enterica* serovar Typhimurium. It is another object of this invention that this novel, mutated *S. enterica* serovar Typhimurium is a live attenuated bacteria or an inactivated bacteria.

It is another object of this invention to have a kit containing antigen which can be at least one novel, mutated *S. enterica* serovar Typhimurium, a bacterial ghost of thereof, or a membrane fraction thereof; a pharmaceutically acceptable carrier or diluent, instructions for use, and optionally an adjuvant. It is a further object of this invention that the novel, mutated *S. enterica* serovar Typhimurium has at least one mutation in at least one gene involved in LPS synthesis and at least one mutation in at least one sRNA gene selected from the group consisting of rybB, micA, omrA, omrB, and invR. In other embodiments, the novel, mutated *S. enterica* serovar Typhimurium has at least one null mutation in each of rfaH, rybB, micA, omrA, omrB, and invR. In another embodiment, the *S. enterica* serovar Typhimurium is strain BBS 866 which is Patent Deposit Accession Number NRRL B-50989. In another embodiment, the *S. enterica* serovar Typhimurium is strain BBS 1134 which is Patent Deposit Accession Number NRRL B-50990. It is another object of this invention that this novel, mutated *S. enterica* serovar Typhimurium is a live attenuated bacteria or an inactivated bacteria.

It is an object of this invention to have a novel, mutated *S. enterica* serovar Typhimurium having a null mutation in omrA and omrB. In some embodiments, the novel, mutated *S. enterica* serovar Typhimurium also has a null mutation in at least one of rybB, micA, and invR, or a combination thereof. In other embodiments, the novel, mutated *S. enterica* serovar Typhimurium has null mutations in rybB, micA, invR, omrA, and omrB. It is another object of this invention that this novel, mutated *S. enterica* serovar Typhimurium is a live attenuated bacteria or an inactivated bacteria. In one embodiment of this invention, the novel, mutated *S. enterica* serovar Typhimurium is a bacterial ghost or membrane fractions of this novel, mutated *S. enterica* serovar Typhimurium. In another embodiment, the *S. enterica* serovar Typhimurium is strain BBS 866 which is Patent Deposit Accession Number NRRL B-50989. In another embodiment, the *S. enterica* serovar Typhimurium is strain BBS 1134 which is Patent Deposit Accession Number NRRL B-50990.

It is another object of this invention to have a method of preventing or reducing transmission of *S. enterica* from a first animal to a second animal by administering to the first animal an immunologically effective amount of a novel, mutated *S. enterica* serovar Typhimurium, a bacterial ghost of this novel, mutated *S. enterica* serovar Typhimurium, or a membrane fraction of this novel, mutated *S. enterica* serovar Typhimurium, or an immunogenic composition containing a pharmaceutically acceptable carrier and this novel, mutated *S. enterica* serovar Typhimurium, a bacterial ghost thereof, and/or membrane fractions thereof. It is a further object of this invention that the novel, mutated *S. enterica* serovar Typhimurium has at least one mutation in at least one gene involved in LPS synthesis and at least one mutation in at least one sRNA gene selected from the group consisting of rybB, micA, omrA, omrB, and invR. In other embodiments, the novel, mutated *S. enterica* serovar Typhimurium has at least one null mutation in each of rfaH, rybB, micA, omrA, omrB, and invR. In another embodiment, the *S. enterica* serovar Typhimurium is strain BBS 866 which is Patent Deposit Accession Number NRRL B-50989. In another embodiment, the *S. enterica* serovar Typhimurium is strain BBS 1134 which is Patent Deposit Accession Number NRRL B-50990. It is another object of this invention that this novel, mutated *S. enterica* serovar Typhimurium is a live attenuated bacteria or an inactivated bacteria.

Figure 1:
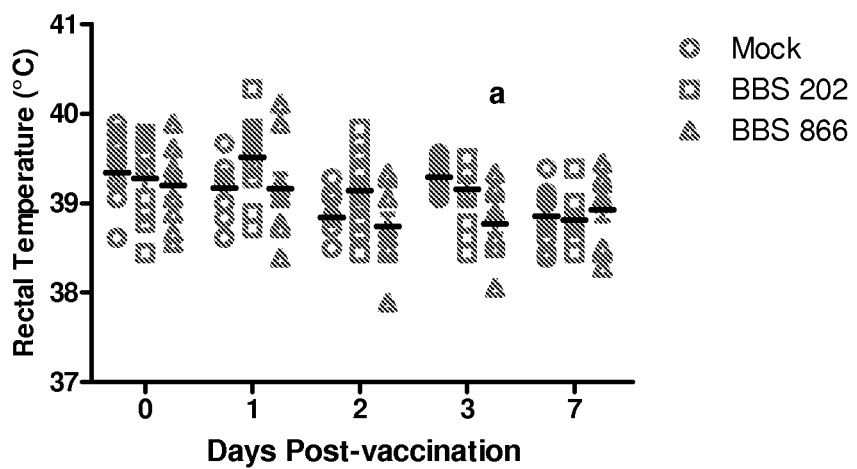
FIG. 1 shows the rectal temperature of swine immunized with either *S. enterica* serovar Typhimurium mutant strain BBS 202 or mutant strain BBS 866 or PBS buffer (mock immunized) at 1, 2, 3, and 7 days after immunization.
Figure 2:
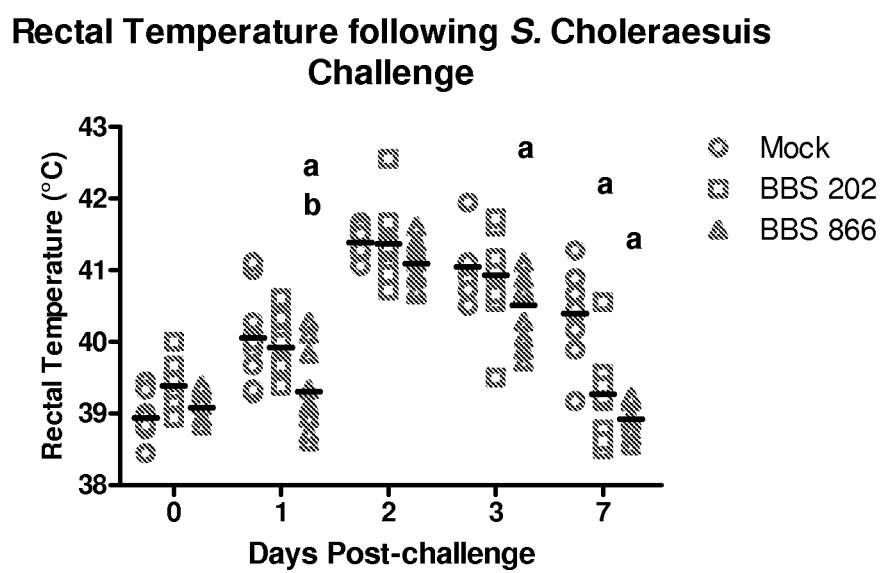
FIG. 2 shows the rectal temperature of swine immunized with either *S. enterica* serovar Typhimurium mutant strain BBS 202 or mutant strain BBS 866 or PBS buffer (mock immunized) at 1, 2, 3, and 7 days after challenge with *S. enterica* serovar Choleraesuis.

STATEMENT REGARDING DEPOSIT OF BIOLOGICAL MATERIAL UNDER THE TERMS OF THE BUDAPEST TREATY

On or before Dec. 2, 2014, the inventors deposited a sample of a mutated *S. enterica* serovar Typhimurium designated strain BBS 866 and a sample of a mutated *S. enterica* serovar Typhimurium designated strain BBS 1134, as described herein, with the U.S.D.A., Agricultural Research Service's Patent Culture Collection located at the National Center for Agricultural Utilization Research, 1815 N. University Street, Peoria, Ill. 61604, in a manner affording permanence of the deposit and ready accessibility thereto by the public if a patent is granted. The deposits have been made under the terms of the Budapest Treaty on the International Recognition of the Deposit of Microorganisms for the Purposes of Patent Procedure and the regulations thereunder. For strain BBS 866, the deposit's accession number is Patent Deposit Accession Number NRRL B-50989, and for strain BBS 1134, the deposit's accession number is Patent Deposit Accession Number NRRL B-50990.

All restrictions on the availability to the public of strain BBS 866 and strain BBS 1134 which have been deposited as described herein will be irrevocably removed upon the granting of a patent covering these particular biological materials.

The mutated *S. enterica* serovar Typhimurium designated strain BBS 866 and strain BBS 1134 have been deposited under conditions such that access to the microorganisms are available during the pendency of the patent application to one determined by the Commissioner to be entitled thereto under 37 C.F.R. §1.14 and 35 U.S.C §122.

The deposited biological materials will be maintained with all the care necessary to keep them viable and uncontaminated for a period of at least five years after the most recent request for the furnishing of a sample of the deposited microorganisms, and in any case, for a period of at least thirty (30) years after the date of deposit for the enforceable life of the patent, whichever period is longer.

We, the inventors for the invention described in this patent application, hereby declare further that all statements regarding this Deposit of the Biological Material made on information and belief are believed to be true and that all statements made on information and belief are believed to be true, and further that these statements are made with knowledge that willful false statements and the like so made are punishable by fine or imprisonment, or both, under section 1001 of Title 18 of the United States Code and that such willful false statements may jeopardize the validity of the instant patent application or any patent issuing thereon.

DETAILED DESCRIPTION OF THE INVENTION

The various mutated *S. enterica* serovar Typhimurium strains of this invention are made using recombinant DNA technology. Administering one or more of the various mutated *S. enterica* serovar Typhimurium strains of this invention to porcine, avian, and other animals causes the animals to generate an immune response which reduces the transmission, colonization, carriage, morbidity, and mortality caused by other *S. enterica* serovars that are animal pathogens as well as transmission, colonization and/or asymptomatic carriage of other *S. enterica* serovars that are pathogenic to humans. Thus, this invention includes the mutated strains of *S. enterica* serovar Typhimurium described herein (whether live or inactivated or bacterial ghosts or membrane fractions; each mutant bacteria being attenuated compared to the wild-type bacteria), immunogenic compositions containing one or more mutated bacteria, the use of the mutated bacteria and/or the immunogenic compositions to induce an immune response against any *S. enterica* serovar in animals, the use of the mutated bacteria and/or the immunogenic compositions to reduce any *S. enterica* serovar carriage, transmission, and colonization, and kits containing the immunogenic composition.

With the goal of developing a *Salmonella* vaccine strain to address animal health and food safety, two mutated *S. enterica* serovar Typhimurium strains are designed and constructed. The vaccine strains are attenuated for pathogenesis in swine, turkeys, and other animals compared to the wild-type *S. enterica* serovar Typhimurium parent strain and provide protection against subsequent challenge with any *S. enterica* serovar. These mutated *S. enterica* serovar Typhimurium strains have two general types of mutations. One type of mutation involves a decreased ability in the production of LPS (lipopolysaccharide). The other type of mutation involves one or more mutations to one or more regulatory small RNA genes (sRNA). In particular, one mutated *S. enterica* serovar Typhimurium is strain BBS 866 (see Table 2 below) has null mutations in rfaH, rybB, omrA, omrB, micA, and invR, and contains genes encoding for resistance to nalidixic acid and kanamycin. *S. enterica* serovar Typhimurium strain BBS 1134 is identical to strain BBS 866, except that the neo gene which confers kanamycin resistance has been removed. Thus, one of ordinary skill in the art would expect strain BBS 1134 to produce the same immunogenic response in animals as strain BBS 866.

As mentioned previously, LPS mutations reduce or prevent LPS synthesis. Many genes are involved in the production of LPS and can be mutated to disrupt or alter LPS synthesis. Non-limited examples of such genes include rfaH (Nagy, et al., *Infect. Immun.* 74(10):5914-5925 (2006) and Nagy, et al., *Infect. Immun.* 72(7):4297-4301 (2004)); relA (Ishiguro, et al., *J. Bacteriol.* 168(1):328-33 (1986)); galE (Potter and Lo, *Infect. Immun.* 64(3):855-60 (1996)); rfb (Hone, et al., *Mol. Microbiol.* 13(3):525-30 (1994)) and pmi (Narasaki, et al. *PLoS One* 6(10):e25514 (2011)). The mutated *S. enterica* serovar Typhimurium of the present invention can contain any known in the art mutation that stops or reduces LPS synthesis, including but not limited, to rfaF, rfaG, rfaI, rfaH, rfaJ, rfaL, and rfbA (see U.S. App. 2013-0052230 Boyen, et al.). In the examples infra, the mutant *S. enterica* serovar Typhimurium contains a null mutation (mRNA is not transcribed or the gene product is not translated) in rfaH, thereby reducing or eliminating LPS production. The RfaH antiterminator prevents the premature termination of long mRNA transcripts encoded by large operons including rfa and rfb involved in LPS core and O-antigen synthesis, respectively. The greater than 2,400 *Salmonella* serovars vary in part because of the O-antigen located on the bacterial outer membrane. Pathogen colonization and infection of a host stimulates an immune response to the O-antigen on the outer membrane of the particular *Salmonella* serovar. However, this immune response may only provide limited protection against other *Salmonella* serovars that express different O-antigens. Not wishing to be bound to any hypothesis, the mutation of rfaH in *S. enterica* serovar Typhimurium decreases LPS core and O-antigen synthesis in the bacteria which is believed to expose outer membrane proteins that may be conserved in *Salmonella* spp. and related Enterobacteriaceae.

The mutated *S. enterica* serovar Typhimurium of the present invention also contain null mutations in one or more of the following sRNA genes: omrA, omrB, rybB, micA, and invR. sRNAs are involved in many physiological processes in the bacterial cell, including but not limited to, regulation of transcription factors, virulence genes, protein metabolism, and quorum sensing. See, e.g., Vogel and Papenfort, *Current Opinion in Microbiology*, 9:605-611 (2006); Papenfort and Vogel, *Cell Host and Microbe* 8:116-127 (2010); and Hebrard, et al., *RNA Biology* 9(4):437-445 (2012). While the role of individual sRNAs in specific bacterial species have been elucidated, it is unknown if the sRNA homologs in other bacterial species possess the identical function. So, while mutations of omrA, omrB, rybB, and micA have been described in *Escherichia coli*, it is unknown if null mutations in the *S. enterica* homologs would result in an identical phenotype, or if a *S. enterica* serovar Typhimurium containing the mutations would generate cross-reactivity for other *S. enterica* serovars. Not wishing to be bound to any particular hypothesis, it is believed that the null mutations in omrA, omrB, rybB, micA, and/or invR increase the production of conserved outer membrane proteins which increases the efficacy and cross-protective capabilities of the mutated *S. enterica* serovar Typhimurium of the present invention. In particular, OmrA and OmrB sRNAs decrease the steady-state levels of multiple mRNA targets that encode outer membrane proteins including cirA, ompT, fepA, and fecA.

It is a surprising and unexpected result that a mutant *S. enterica* serovar Typhimurium containing both a mutation in LPS synthesis and one or more mutations to omrA, omrB, rybB, micA, and/or invR provides better results than *S. enterica* serovar Typhimurium containing the individual mutations. Whatever the actual causative effects of these mutations, the mutated bacteria described herein result in an enhanced immune response against a broad repertoire of *Salmonella enterica* serovars that share common, conserved antigens to which an animal may be exposed during its lifetime. Furthermore, utilization of these attenuated bacterial strains in other animal and avian species also confer increased, and perhaps protective, immunity against *Salmonella* spp. and other Enterobacteriaceae thereby reducing gastrointestinal colonization, pathogen fecal shedding, and disease severity caused by these bacteria.

While the examples below discuss generation of deletion mutations in these genes, one of ordinary skill in the art could use other types of mutations in these genes (such as point mutations) which would result in identical phenotypes. This invention is not limited to bacteria containing deletion mutations in these identified genes. Rather the invention includes any mutation in the identified genes that result in the described phenotype. Furthermore, these mutated *S. enterica* serovar Typhimurium have an attenuated phenotype compared to the wild-type *S. enterica* serovar Typhimurium which enables one to administer live, attenuated *S. enterica* serovar Typhimurium to the animal. In addition to an attenuated *S. enterica* serovar Typhimurium having at least one mutation in a gene involving LPS production and at least one mutation in rybB, micA, omrA, omrB, and/or invR, the present invention includes an inactivated *S. enterica* serovar Typhimurium having at least one mutation in a gene involving LPS production and at least one mutation in rybB, micA, omrA, omrB, and/or invR, bacterial ghost of *S. enterica* serovar Typhimurium having at least one mutation in a gene involving LPS production and at least one mutation in rybB, micA, omrA, omrB, and/or invR, and preparations containing membrane proteins which are produced by an *S. enterica* serovar Typhimurium having at least one mutation in a gene involving LPS production and at least one mutation in rybB, micA, omrA, omrB, and/or invR. To generate an inactivated mutated *S. enterica* serovar Typhimurium, one simply kills the live, attenuated *S. enterica* serovar Typhimurium after growing the bacteria to the desired density. Inactivation can occur via application of heat, a cross-linking agent (e.g., formaldehyde), UV irradiation, or similar types of chemicals or environmental treatments. Bacterial ghosts are a specific type of inactivated bacteria, namely cell envelopes created by controlled bacterial cell lysis. One method is the expression of a recombinant lysis gene obtained from a phage, such as gene E from phage φX174. E is a small protein that forms a pore in the bacterial cell membrane, allowing all cytoplasmic content to flow out of the bacteria, thereby killing the bacteria but leaving the cell with a preserved cellular morphology including all cell surface structures. Other methods for creating bacterial ghosts could be performed by one of ordinary skill in the art. Bacterial ghosts exhibit intrinsic adjuvant properties and trigger an enhanced humoral and cellular immune response to the target antigen. The mutated S. enterica serovar Typhimurium can contain gene E under control of an inducible promoter and be fermented normally. Upon addition of the inducing agent, E is produced and the mutated bacteria become inactivated ghosts. The bacterial ghosts can be isolated and purified from the fermenter using tangential flow filtration or other known in the art techniques. Preparations containing bacterial proteins associated with the outer membrane can be made using well-known in the art techniques. One such technique is described in U.S. Pat. No. 6,432,412. These preparations are referred herein as "membrane fractions".

Because this invention involves production and purification of mutated bacteria that may be administered to an animal, and because this invention involves recombinant DNA techniques, the following definitions are provided to assist in describing this invention. The terms "isolated", "purified", or "biologically pure" as used herein, refer to material that is substantially or essentially free from components that normally accompany the material in its native state or when the material is produced. In an exemplary embodiment, purity and homogeneity are determined using analytical chemistry techniques such as polyacrylamide gel electrophoresis or high performance liquid chromatography. A nucleic acid or particular bacteria that are the predominant species present in a preparation is substantially purified. In an exemplary embodiment, the term "purified" denotes that a nucleic acid or protein that gives rise to essentially one band in an electrophoretic gel. Typically, isolated nucleic acids or proteins have a level of purity expressed as a range. The lower end of the range of purity for the component is about 60%, about 70% or about 80% and the upper end of the range of purity is about 70%, about 80%, about 90% or more than about 90%.

The term "nucleic acid" as used herein, refers to a polymer of ribonucleotides or deoxyribonucleotides. Typically, "nucleic acid" polymers occur in either single- or double-stranded form, but are also known to form structures comprising three or more strands. The term "nucleic acid" includes naturally occurring nucleic acid polymers as well as nucleic acids comprising known nucleotide analogs or modified backbone residues or linkages, which are synthetic, naturally occurring, and non-naturally occurring, which have similar binding properties as the reference nucleic acid, and which are metabolized in a manner similar to the reference nucleotides. Exemplary analogs include, without limitation, phosphorothioates, phosphoramidates, methyl phosphonates, chiral-methyl phosphonates, 2-O-methyl ribonucleotides, and peptide-nucleic acids (PNAs). "DNA", "RNA", "polynucleotides", "polynucleotide sequence", "oligonucleotide", "nucleotide", "nucleic acid", "nucleic acid molecule", "nucleic acid sequence", "nucleic acid fragment", and "isolated nucleic acid fragment" are used interchangeably herein.

For nucleic acids, sizes are given in either kilobases (kb) or base pairs (bp). Estimates are typically derived from agarose or acrylamide gel electrophoresis, from sequenced nucleic acids, or from published DNA sequences. For proteins, sizes are given in kilodaltons (kDa) or amino acid residue numbers. Proteins sizes are estimated from gel electrophoresis, from sequenced proteins, from derived amino acid sequences, or from published protein sequences.

The term "recombinant" when used with reference, e.g., to a cell, or nucleic acid, protein, or vector, indicates that the cell, organism, nucleic acid, protein or vector, has been modified by the introduction of a heterologous nucleic acid or protein or the alteration of a native nucleic acid or protein, or that the cell is derived from a cell so modified. Thus, for example, recombinant cells may express genes that are not found within the native (non-recombinant or wild-type) form of the cell or express native genes that are otherwise abnormally expressed—over-expressed, under-expressed or not expressed at all.

The terms "transgenic", "transformed", "transformation", and "transfection" are similar in meaning to "recombinant". "Transformation", "transgenic", and "transfection" refer to the transfer of a polynucleotide into the genome of a host organism or into a cell. Such a transfer of polynucleotides can result in genetically stable inheritance of the polynucleotides or in the polynucleotides remaining extra-chromosomally (not integrated into the chromosome of the cell). Genetically stable inheritance may potentially require the transgenic organism or cell to be subjected for a period of time to one or more conditions which require the transcription of some or all of the transferred polynucleotide in order for the transgenic organism or cell to live and/or grow. Polynucleotides that are transformed into a cell but are not integrated into the host's chromosome remain as an expression vector within the cell. One may need to grow the cell under certain growth or environmental conditions in order for the expression vector to remain in the cell or the cell's progeny. Further, for expression to occur the organism or cell may need to be kept under certain conditions. Host organisms or cells containing the recombinant polynucleotide can be referred to as "transgenic" or "transformed" organisms or cells or simply as "transformants", as well as recombinant organisms or cells.

This invention utilizes routine techniques in the field of molecular biology. Basic texts disclosing the general methods of use in this invention include Green and Sambrook, 4th ed. 2012, Cold Spring Harbor Laboratory; Kriegler, *Gene Transfer and Expression: A Laboratory Manual* (1993); and Ausubel et al., eds., *Current Protocols in Molecular Biology*, 1994—current, John Wiley & Sons. Unless otherwise noted, technical terms are used according to conventional usage. Definitions of common terms in molecular biology may be found in e.g., Benjamin Lewin, *Genes IX*, published by Oxford University Press, 2007 (ISBN 0763740632); Krebs, et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

An "immunogenic composition" is a composition that contains an antigen where administration of the composition to an animal results in an immune response. In this invention, the antigen is the mutated *Salmonella enterica* serovar Typhimurium described herein which has an attenuated phenotype compared to the wild-type *S. enterica* serovar Typhimurium. The attenuating phenotype is caused by at least one mutation in a gene involving LPS production Immunogenic compositions of this invention can contain a live, attenuated mutated *S. enterica* serovar Typhimurium with the mutation(s) described herein, an inactivated *S.*

*enterica* serovar Typhimurium containing the mutation(s) described herein; membrane fractions derived from the *S. enterica* serovar Typhimurium containing the mutation(s) described herein; and/or a bacterial ghost of the mutated *S. enterica* serovar Typhimurium described herein; along with one or more pharmaceutically acceptable diluents, carriers, and/or adjuvants. Additional antigens can also be included in the immunogenic compositions such as the use of the *S. enterica* serovar Typhimurium containing the mutation(s) described herein as a vector for the delivery and/or expression of antigens, therapeutic DNA, therapeutic proteins, immunoregulatory agents, and/or antisense RNAs into an animal via eukaryotic or prokaryotic expression vectors contained within the *S. enterica* serovar Typhimurium of this invention (see U.S. Pat. No. 6,150,170 describing an attenuated *Shigella* as a carrier of an eukaryotic expression vector). The immunogenic composition can also be a combination of an animal feed or water and the mutated *S. enterica* serovar Typhimurium, membrane fractions, and/or bacterial ghosts described herein. Such an immune response in the animal may be a humoral and/or a cellular immune response to the antigen. The antigen is also referred herein as an "immunogenic agent".

An "immunological response" or "immune response" to an antigen or immunogenic composition is, in an animal, the development, increase, or decrease of a humoral and/or a cellular immune response to the antigen or antigen present in the immunogenic composition. The immune response may be an increased or enhanced immune response (immunostimulatory) or a decrease or suppression of an immune response (immuno-suppressant). The immune response may be a systemic and/or localized immune response. For the present invention, a "humoral immune response" refers to an immune response mediated by antibody molecules, while a "cellular immune response" is one mediated by T-lymphocytes and/or other white blood cells.

One important aspect of cellular immunity or cellular immune response involves an antigen-specific response by cytolytic T-cells ("CTL" or "CTLs"). CTLs have specificity for peptide antigens that are presented in association with proteins encoded by the major histocompatibility complex ("MHC") and which are expressed on the surfaces of cells. CTLs induce and promote the destruction of intracellular microbes, or the lyses of cells infected with such microbes. Another aspect of cellular immune response involves an antigen-specific response by helper T-cells (Th cells). Th cells act to help stimulate the function, and focus the activity of, nonspecific effector cells against cells displaying peptide antigens in association with MHC molecules on their surface. A cellular immune response also refers to the production of cytokines, chemokines and other such molecules produced by activated T-cells and/or other white blood cells, including those derived from CD4+ and CD8+ T-cells.

Th cells include Th1 cells and/or Th2 cells. A Th1 cell immune response may include one or more of the following: an increase in CD8+ CTLs; an increase in one or more of the cytokines associated with a Th1 cell immune response (such as interleukin 12 (IL-12), interferon gamma (IFN-γ), and tumor necrosis factor beta (TNF-β)); an increase in activated macrophages; an increase in NK activity; and/or an increase in the production of $IgG_{2a}$. In one embodiment, the enhanced Th1 cell immune response will include an increase in IL-12 and $IgG_{2a}$ production. Activated Th2 cells enhance antibody production and are therefore of value in responding to certain types of extracellular infections. Activated Th2 cells may secrete one or more of IL-4, IL-5, IL-6, and IL-10. A Th2 cell immune response may result in the production of $IgG_1$, IgE, IgA and memory B cells for future protection.

The ability of a particular antigen to stimulate a cell-mediated immunological response may be determined by a number of assays, such as by lymphoproliferation (lymphocyte activation) assays, CTL assays, or by assaying for T-lymphocytes specific for the antigen in a sensitized subject. Such assays are well known in the art. See, e.g., Erickson, et al., *J. Immunol.* 151:4189-4199 (1993); Doe, et al., *Eur. J. Immunol.* 24:2369-2376 (1994). Recent methods of measuring cell-mediated immune response include measurement of intracellular cytokines or cytokine secretion by T-cell populations, or by measurement of epitope specific T-cells (e.g., by the tetramer technique)(reviewed by McMichael and O'Callaghan, *J. Exp. Med.* 187(9) 1367-1371 (1998); Mcheyzer-Williams, et al., *Immunol. Rev.* 150:5-21 (1996); Lalvani, et al., *J. Exp. Med.* 186:859-865 (1997)).

A humoral immune response is one that stimulates the production of antibodies (e.g., neutralizing antibodies that block bacterial toxins and pathogens, such as viruses, bacteria, fungi, and parasites, from entering cells and replicating by binding to toxins and/or the pathogens, typically protecting cells from infection and destruction). Hence, an immunological response may include one or more of the following effects: the production of antibodies by B-cells; and/or the activation of suppressor T-cells and/or memory/effector T-cells directed specifically to an antigen or antigens present in the immunogenic composition or vaccine. These responses may serve to neutralize infectivity, and/or mediate antibody-complement, or antibody dependent cell cytotoxicity (ADCC) to provide protection to an immunized subject. Such responses can be determined using standard immunoassays and neutralization assays, well known in the art. See, e.g., Montefiori, et al., *J. Clin Microbiol.* 26:231-235 (1988); Dreyer, et al., *AIDS Res. Hum. Retroviruses* 15(17):1563-1571 (1999). The innate immune system of an animal also recognizes and responds to molecular features of pathogenic organisms via activation of Toll-like receptors and similar receptor molecules on immune cells. Upon activation of the innate immune system, various non-adaptive immune response cells are activated to, e.g., produce various cytokines, lymphokines and chemokines. Cells activated by an innate immune response include immature and mature dendritic cells, as well as gamma, delta, alpha and beta T cells and B cells and the like. Thus, the present invention also contemplates an immune response wherein the immune response involves both an innate and adaptive response.

"Vaccination", "vaccinate", "immunization", "immunize", and "inoculate" are synonymous and are the administration of the antigen (the mutated *S. enterica* serovar Typhimurium described herein) or immunogenic composition (containing the mutated *S. enterica* serovar Typhimurium described herein) to the animal Immunization can also include removing immunological cells from the animal, allowing such immunological cells to interact with an antigen in-vitro, and then returning those immunological cells or their progeny back to the animal's body. Exemplary routes of administration of an antigen or immunogenic composition of this invention include, but not limited to, intramuscular injection, intraperitoneal injection, subdermal injection, intradermal injection, subcutaneous injection, intravenous injection, oral administration, sublingual administration, vaginal administration, rectal administration, transmucosally, transcutaneous adsorption, intranodal administration, intracoronary administration, intraarterial administration, intratracheal administration, intraarticular administration, intraventricular administration, intracranial administration, intraspinal administration, intraocular administration, aural administration, inhalation, and intranasal administration. For this invention, oral administration may involve an animal eating the plant or plant cells which contain the antigen, a combination of animal feed and an immunogenic composition containing the mutated *S. enterica* serovar Typhimurium, bacterial ghosts, and/or membrane fractions. These bacterial components can be mixed together with the feed, sprinkled onto the animal feed, or coating the animal feed. Oral administration also includes the animal drinking a liquid containing the mutated *S. enterica* serovar Typhimurium, bacterial ghosts, or membrane fractions. Any suitable liquid (e.g., water) can be used. Such oral administration may result in mucosal immunity to the pathogen against which the antigen is directed. Vaccination and immunization involves inducing an immune response in the animal receiving the antigen or immunogenic composition.

The appropriate dose of the immunogenic composition of the present invention depends on several variables such as the formulation, the route of administration, the animal's age, the animal's weight, the time of administration, the excretion rate, and reaction irritability. One of ordinary skill in the art can determine the appropriate dose by administering the antigen to the animal and assaying for an increase or, if applicable, a decrease in the immune response.

For immunogenic compositions and antigens, "treatment" refers to any of (i) the prevention of infection or reinfection, as in a traditional vaccine, (ii) the reduction or elimination of symptoms, (iii) the substantial or complete elimination of the pathogen in question, (iv) an enhanced immune response to the antigen or immunogenic composition administered to the animal, and/or (v) the reduction of a hypersensitive immune response in the animal. Treatment may be effected prophylactically (prior to infection or exposure to the antigen or infectious agent) or therapeutically (following infection or exposure to the antigen or infectious agent).

One method of assessing efficacy of an immunogenic composition involves monitoring an infection after administration of the immunogenic composition. One method of assessing efficacy of prophylactic administration of the immunogenic composition involves monitoring immune responses against the antigens in the immunogenic composition after administration of the immunogenic composition. Another method of assessing the immunogenicity of the antigens of the immunogenic composition is to express the antigens recombinantly and to screen an animal's sera or mucosal secretions by immunoblot. A positive reaction between the antigen and the animal's serum indicates that the animal previously mounted an immune response to the antigen in question—that is, the antigen is an immunogen. This method may also be used to identify immunodominant proteins and/or epitopes.

Another method involves intentionally infecting the vaccinated animal or allowing the vaccinated animal to be in the presence of infected, non-vaccinated animals and monitoring for symptoms of illness. Alternatively, one may monitor immune responses both systemically (such as monitoring the level of $IgG_1$ and $IgG_{2a}$ production) and mucosally (such as monitoring the level of IgA production) against the antigens in the immunogenic composition after administration of the immunogenic composition. Typically, serum specific antibody responses are determined post-immunization but pre-challenge, whereas mucosal specific antibody responses are determined post-immunization and post-challenge. Other techniques for monitoring the efficacy of the mutated *S. enterica* serovar Typhimurium described herein and the immunogenic compositions containing the mutated *S. enterica* serovar Typhimurium described herein are described in the examples, below, such as changes in body temperature, changes in fecal shedding of bacteria, and the presence of challenge bacteria in certain body parts.

The immunogenic compositions of the present invention can be evaluated in-vitro and in-vivo (i.e., in animal models) or ex-vivo prior to administration to the intended animal. For humans, a particularly useful model is intraperitoneal immunization of a mouse followed by either intraperitoneal challenge or intranasal challenge. The efficacy of an immunogenic composition can also be determined using a challenge animal model of infection. That is, the immunogenic composition may be administered to an animal which is then challenged with the infectious agent. Of course, the immunogenic composition may or may not be derived from the same strain of the infectious agent used in the challenge model.

Immunogenic compositions of the present invention may be used either alone or in combination with other antigens and/or optionally with an immunoregulatory agent ("adjuvant") capable of eliciting a Th1 and/or Th2 response. An immunogenic composition of this invention may contain the antigens of this invention with one or more adjuvants. Non-limiting examples of adjuvants include oil-in-water emulsion, water-in-oil-in-water emulsion, aluminum hydroxide, aluminum phosphate, squalene and squalene-like compounds, Freund's complete adjuvant, Freund's incomplete adjuvant, muramyl dipeptide, monophosphoryl lipid A, polyphosphazine, *E. coli* LT (or LT-B, native or toxoid), *Vibrio cholera* toxin (CTX or CT), CpG motif containing oligonucleotide, and compounds that interact with Toll-like Receptors (TLR). Adjuvants which are capable of preferential stimulation of the Th1 cell response are described in International Patent Application No. WO 94/00153 and WO 95/17209.

The invention also provides for the immunogenic composition described herein to be used as a medicament. A medicament is preferably able to generate an immune response in an animal. The invention also provides for the use of the immunogenic composition of the invention in the manufacture of a medicament for generating an immune response in an animal. In one embodiment, the medicament is a vaccine or an immunostimulatory composition or an immunosuppressant composition.

The invention provides methods for inducing or increasing an immune response using the immunogenic composition. The immune response is preferably protective and can include antibodies and/or cell-mediated immunity (including systemic and mucosal immunity). Immune responses include booster responses. The invention also provides methods for suppressing or decreasing an immune response in the animal to the antigen using an immunogenic composition. Such a suppression of an immune response may be useful if the animal is hypersensitive to the antigen.

A prophylactic antigen or prophylactic immunogenic composition can be administered to the animal, especially to young animals, to pregnant animals, and to elderly animals. The age of the young animal will vary depending on the animal's lifespan and if the young has maternal antibodies upon birth or, if the animal is a mammal, obtains maternal antibodies during nursing. Administering a prophylactic immunogenic composition to a pregnant animal may help stimulate the immune response of the fetus or baby animal prior to and shortly after birth. It may also stimulate the pregnant animal's immune system thereby improving the pregnant animal's health. Of course, administering prophylactic compositions to an elderly animal may boost the elderly animal's immune system to the antigen contained with the composition and thus help prevent the elderly animal from being infected with the bacteria, virus, or parasite containing the antigen. Administering an immunosuppressant composition would be considered a prophylactic administration in that one desires to reduce the animal's response to the antigen contained in the immunosuppressant composition prior to the animal's next exposure to the antigen.

The invention also includes kits containing one or more containers of the immunogenic compositions and/or antigens of the invention. The immunogenic composition can be in liquid form or can be lyophilized; as can be the antigens. Suitable containers for the immunogenic compositions and/or antigens include, for example, bottles, jugs, vials, syringes, and test tubes. Containers can be formed from a variety of materials, including glass or plastic. A container may have a sterile access port (for example, the container may be an intravenous solution bag or a vial having a stopper pierceable by a hypodermic injection needle). The kit can also contain a second container inside of which is a pharmaceutically-acceptable buffer, such as phosphate-buffered saline, Ringer's solution, or dextrose solution. The kit can also contain other materials useful to the end-user, including other pharmaceutically acceptable formulating solutions such as buffers and/or diluents, filters, needles, and syringes or other delivery devices. The kit may optionally include an adjuvant in a container. The kit can also contain written instructions for administering the immunogenic composition and/or antigen and other contents of the kits to subjects. The written instructions may describe methods for inducing an immune reaction or methods for treating infections. The invention also includes a delivery device prefilled with the immunogenic composition of the invention.

The immunogenic agent may be prepared for administration by formulating an effective immunization dosage of the antigen with a pharmaceutically acceptable carrier or diluent, such as physiological saline or tissue culture medium. The expression "effective immunization dosage" is that amount which will induce immunity in an animal against challenge using the infectious agent or that amount which will induce immunity in an animal against a challenge with the infectious agent against which the antigen is directed Immunity is considered as having been induced in an animal when the level of protection for the animal is significantly higher than that of an unvaccinated control group.

The immunogenic composition of this invention may contain one or more pharmaceutically acceptable carriers. Non-limited examples of such carriers include lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methyl cellulose, methyl hydroxy benzoate, propyl hydroxy benzoate, talc, stearic acid, magnesium, and mineral oils. In addition to the above ingredients of the pharmaceutical composition according to the present invention may further comprise lubricants, wetting agents, sweetening agents, flavoring agents, emulsifiers, suspending agents, preservatives, etc. Suitable pharmaceutically acceptable carriers and formulations are described in detail in *Remington's Pharmaceutical Sciences* (19th ed., 1995). Because the immunogenic compositions of the present invention can be used in both animals and humans, "pharmaceutically accept-able" refers to those items, compounds, etc. that are approved for use in human and/or in animals.

The examples herein describe the administration of the mutated *S. enterica* serovar Typhimurium to pigs and to turkeys. However, this invention is not limited to inducing an immune response in porcine and turkeys. Rather, this invention described herein may be administered to bovine, equine, ovine, goats, and any other mammals including humans; birds (including but not limited to chickens, turkeys, quail, ducks, and other domesticated birds); amphibians; reptiles; and fish. This invention can include any animal for which it is desirous to reduce the animal's carriage, colonization and/or transmission of *Salmonella enterica* serovars, or to prevent or reduce illness caused by *Salmonella enterica* serovars, or to induce an immune response against *Salmonella enterica* serovars. For this invention, the term "subject" is used to cover any animal.

Example 1

Construction of Mutated *Salmonella enterica* Serovar Typhimurium Strains

The mutated strains of *S. enterica* serovar Typhimurium are constructed using recombinant DNA techniques as described previously (Bearson, et al., *Microbes and Infection* 10:807-816 (2008)). To construct the specific gene knockout mutants, ~1.2 kb linear DNA fragments containing the neomycin resistance gene (neo) are generated by PCR. The nucleotide sequences of each primer pair used in these PCR reactions are shown in Table 1. The ~1.2 kb linear DNA fragments containing neo are flanked at their 5' and 3' ends with 39-46 nucleotides of DNA sequence corresponding to the upstream and downstream nucleotide sequence for a particular target gene. Each pair of knockout primers for a particular gene contains a nucleotide sequence on the 5' end that is homologous to the target gene of interest (bold) and a sequence on the 3' end (underlined) that binds to the oBBI 92/93 neo template for PCR amplification.

TABLE 1

| Target gene | Primer | Primer Nucleotide Sequence (5'→3') |
|---|---|---|
| rfaH | oBBI 189 (forward) | atgcaatcctggtatttactgtactgcaaacgcgggcaacttcagcatagagcagtgacgtagtcgc SEQ ID NO: 1 |
| rfaH | oBBI 190 (reverse) | ctaaatcttgcgaaaaccggtgtttttttacgctctgcttcacttcgatagctgaatgagtgacgtgc SEQ ID NO: 2 |
| rybB | oBBI 378 (forward) | ctgaagtttgcctttaagtgaaaaaattttgccaataggtcgatagctgaatgagtgacgtgc SEQ ID NO: 3 |
| rybB | oBBI 379 (reverse) | caaaaaacccaccaaccttgaaccgaaatggcggggttgatgggcatagagcagtgacgtagtcgc SEQ ID NO: 4 |
| omrAB | oBBI 383 (forward) | gattacacgagttgcgtaacaggagcgatagcaaaataggttcgatagctgaatgagtgacgtgc SEQ ID NO: 5 |
| omrAB | oBBI 384 (reverse) | caaatctttcgttacagtttgcgaagcgctgttgcgattgtctgcatagagcagtgacgtagtcgc SEQ ID NO: 6 |
| micA | oBBI 385 (forward) | ctgaactctttgttccggggcgagtctgagtatatgaaagacgatagctgaatgagtgacgtgc SEQ ID NO: 7 |

TABLE 1-continued

| Target gene | Primer | Primer Nucleotide Sequence (5'→3') |
|---|---|---|
| micA | oBBI 386 (reverse) | cgtggcttgcaaaacacgcctgacccaa aagaaaaaggcatagagcagtgacgtag tcgc SEQ ID NO: 8 |
| invR | oBBI 408 (forward) | ctgaactcatcatgatataattaagacc atattttgcattgccacgatagctgaat gagtgacgtgc SEQ ID NO: 9 |
| invR | oBBI 409 (reverse) | ccaagtctgggaggccgttctttatcac aaataaaaaagcatagagcagtgacgt agtcgc SEQ ID NO: 10 |

Following PCR amplification of the oBBI 92/93 neo template with a given primer set, gel electrophoresis is performed using a 1% agarose gel in TBE, and the PCR fragment is excised from the gel and purified using a BioRad Freeze'n Squeeze column according to manufacturer's recommendations (Hercules, Calif.). The linear knockout fragment containing the neo gene is electroporated into arabinose-induced competent cells of S. enterica serovar Typhimurium BSX 7 or BBS 209 containing the plasmid pKD46 encoding Lambda exo, bet, and gam to facilitate recombination of the linear DNA fragment using the protocol described in Datsenko and Wanner, Proc. Natl. Acad. Sci. USA 97:6640-6645 (2000). Kanamycin-resistant transformants are screened by PCR to confirm the replacement of the target gene with the neo gene. Gene knockout mutations are transferred to other S. enterica serovar Typhimurium mutant strains using P22 high-transducing phage lysates grown on the kanamycin-resistant donor strain. The oBBI 92/93 neo cassette contains FRT sequences for enabling a FLP catalyzed deletion of neo (Bearson, et al., Microbes and Infection 10:807-816 (2008)). The plasmid pCP20, encoding FLP recombinase, is transferred to the kanamycin-resistant knockout mutants by transformation with purified plasmid from EBB 221 or P22 phage transduction from BBS 120, and the recipient strains are grown at 30° C. (Cherepanov and Wackernagel, Gene 158:9-14 (1995)). The gene deletion mutants are constructed using FLP recombinase to facilitate deletion of the neo gene followed by loss of the temperature-sensitive pCP20 plasmid when the gene deletion mutant is grown at 37° C. Following strain construction, bacterial strains are assigned BBS designations (see Table 2) and stored at −80° C. in stocking solution containing 0.9% saline and 15% glycerol.

TABLE 2

| Strain | Parent Strain | Genotype | Phenotype | Notes |
|---|---|---|---|---|
| EBB 221 | TOP10 | F- mcrA Δ(mrr-hsdRMS-mcrBC) Phi80lacZΔM15 ΔlacX74 recA1 araD139 Δ(ara-leu)7697 galU galK rpsL (Str$^R$) endA1 nupG/pCP20 | Str$^R$, Cam$^R$, Ap$^R$, 30° C. | Transformation of Top10 with pCP20 containing the FLP recombinase for deletion of antibiotic resistance gene flanked by FRT sites |
| BSX 7 | TT22971 (LT2) | metA22 metE551 trpD2 ilv-452 leu pto (leaky) hsdLT6 hsdSA29 hsdB strA120/pKD46 araC bla oriR101 repA101ts lambda red (gam+ bet+ exo+) | Ap$^R$, 30° C. | grow at 30° C.; Lambda red under Para control |
| BSX 8 | χ4232 | S. enterica serovar Typhimurium | Nal$^R$ | Wild-type |
| BBS 119 | BSX 7 [TT22971 (LT2)] | metA22 metE551 trpD2 ilv-452 leu pto (leaky) hsdLT6 hsdSA29 hsdB strA120 | | Single colony isolation of BSX 7 grown at 37° C., cured of pKD46, Ap$^S$ |
| BBS 120 | BSX 7 [TT22971 (LT2)] | metA22 metE551 trpD2 ilv-452 leu pto (leaky) hsdLT6 hsdSA29 hsdB strA120/pCP20 | Ap$^R$, 30° C. | Electroporation of BBS 119 with pCP20 containing the FLP recombinase for deletion of antibiotic resistance gene flanked by FRT sites, pCP20 from EBB 221 |
| BBS 195 | BSX 7 [TT22971 (LT2)] | metA22 metE551 trpD2 ilv-452 leu pto (leaky) hsdLT6 hsdSA29 hsdB strA120 rfaH::neo | Kn$^R$ | Electroporation of arabinose induced BSX 7 with oBBI 189/190 neo |
| BBS 201 | BSX 7 [TT22971 (LT2)] | metA22 metE551 trpD2 ilv-452 leu pto (leaky) hsdLT6 hsdSA29 hsdB strA120 rfaH::neo/ pBADoBBI193/194 | Kn$^R$ Ap$^R$ | Electroporation of BBS 195 with pBADoBBI193/194 (complements rfaH mutation) |
| BBS 202 | BSX 8 (χ4232) | rfaH::neo | Nal$^R$ Kn$^R$ | Transduction of BSX 8 with HT BBS 201 |
| BBS 209 | BSX 8 (X4232) | pKD46 | Nal$^R$ Ap$^R$ 30° C. | Transduction of BSX 8 with HT BSX 7 |
| BBS 782 | BSX 7 [TT22971 (LT2)] | metA22 metE551 trpD2 ilv-452 leu pto (leaky) hsdLT6 hsdSA29 hsdB strA120 rybB::neo | Kn$^R$ | Electroporation of arabinose induced BSX 7 with oBBI 378/379 neo |
| BBS 786 | BSX 7 [TT22971 (LT2)] | metA22 metE551 trpD2 ilv-452 leu pto (leaky) hsdLT6 hsdSA29 hsdB strA120 omrAB::neo | Kn$^R$ | Electroporation of arabinose induced BSX 7 with oBBI 383/384 neo |
| BBS 790 | BSX 8 (χ4232) | rybB::neo | Nal$^R$ Kn$^R$ | Transduction of BSX 8 with HT BBS 782 |
| BBS 805 | BSX 8 (χ4232) | ΔrybB | Nal$^R$ | Transduction of BBS 790 with HT BBS 120 |
| BBS 811 | BSX 8 (χ4232) | ΔrybB omrAB::neo | Nal$^R$ Kn$^R$ | Transduction of BBS 805 with HT BBS 786 |

TABLE 2-continued

| Strain | Parent Strain | Genotype | Phenotype | Notes |
|---|---|---|---|---|
| BBS 814 | BSX 8 (χ4232) | micA::neo | Nal$^R$ Kn$^R$ | Electroporation of arabinose induced BBS 209 with oBBI 385/386 neo |
| BBS 817 | BSX 8 (χ4232) | ΔrybB ΔomrAB | Nal$^R$ | Transduction of BBS 811 with HT BBS 120 |
| BBS 827 | BSX 8 (χ4232) | ΔrybB ΔomrAB micA::neo | Nal$^R$ Kn$^R$ | Transduction of BBS 817 with HT BBS 814 |
| BBS 836 | BSX 8 (χ4232) | ΔrybB ΔomrAB ΔmicA | Nal$^R$ | Electroporation of BBS 827 with pCP20 for deletion of neo gene |
| BBS 849 | BSX 8 (χ4232) | invR::neo | Nal$^R$ Kn$^R$ | Electroporation of arabinose induced BBS 209 with oBBI 408/409 neo |
| BBS 857 | BSX 8 (χ4232) | ΔrybB ΔomrAB ΔmicA invR::neo | Nal$^R$ Kn$^R$ | Transduction of BBS 836 with HT BBS 849 |
| BBS 860 | BSX 8 (χ4232) | ΔrybB ΔomrAB ΔmicA ΔinvR | Nal$^R$ | Electroporation of BBS 857 with pCP20 for deletion of neo gene |
| BBS 866 (NRRL B-50989) | BSX 8 (χ4232) | ΔrybB ΔomrAB ΔmicA ΔinvR rfaH::neo | Nal$^R$ Kn$^R$ | Transduction of BBS 860 with HT BBS 201 |
| BBS 1134 (NRRL B-50990) | BSX 8 (χ4232) | ΔrybB ΔomrAB ΔmicA ΔinvR ΔrfaH | Nal$^R$ | Electroporation of BBS 866 with pCP20 for deletion of neo gene |

Nal$^R$ means nalidixic acid resistant.
Kn$^R$ means kanamycin resistant.
Ap$^R$ means ampicillin resistant.
Cam$^R$ means chloramphenicol resistant.
Str$^R$ means streptomycin resistant.

Figure 3A:
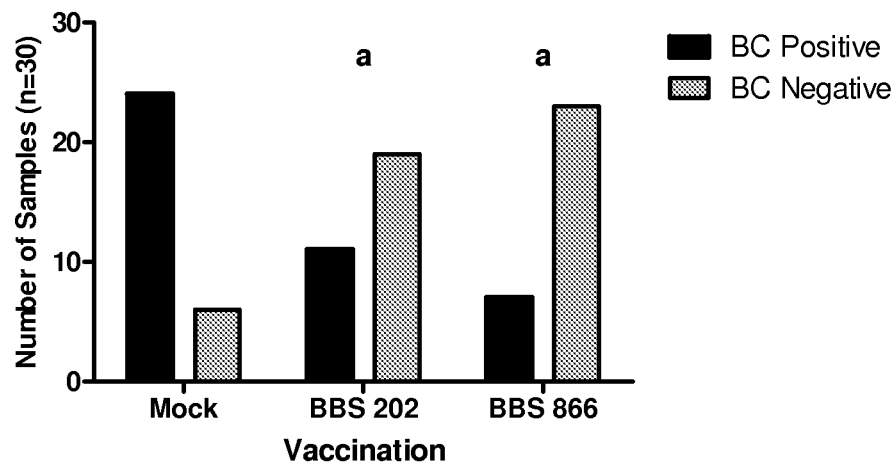
FIG. 3A shows the cumulative blood culture results taken at three time points of porcine immunized with either strain BBS 202 or strain BBS 866 or PBS buffer (mock immunized) and then challenged with *S. enterica* serovar Choleraesuis.
Figure 3B:
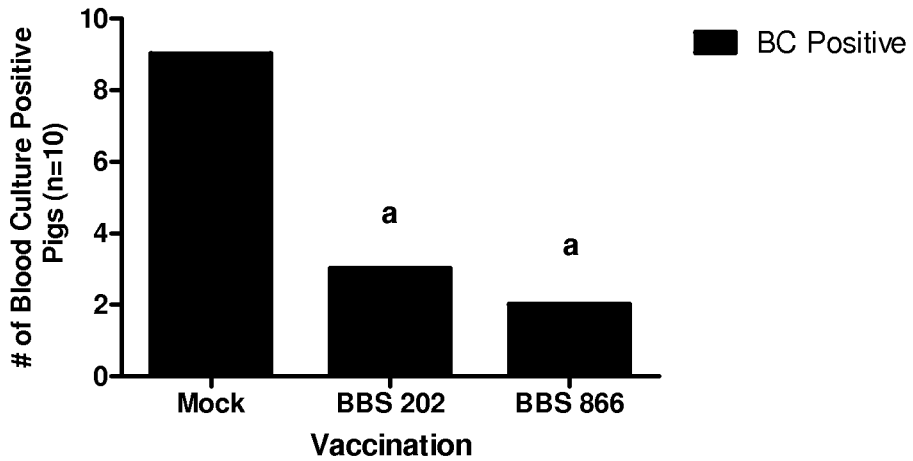
FIG. 3B shows the number of swine blood cultures positive for *S. enterica* serovar Choleraesuis at seven days post-challenge.
Figure 3C:
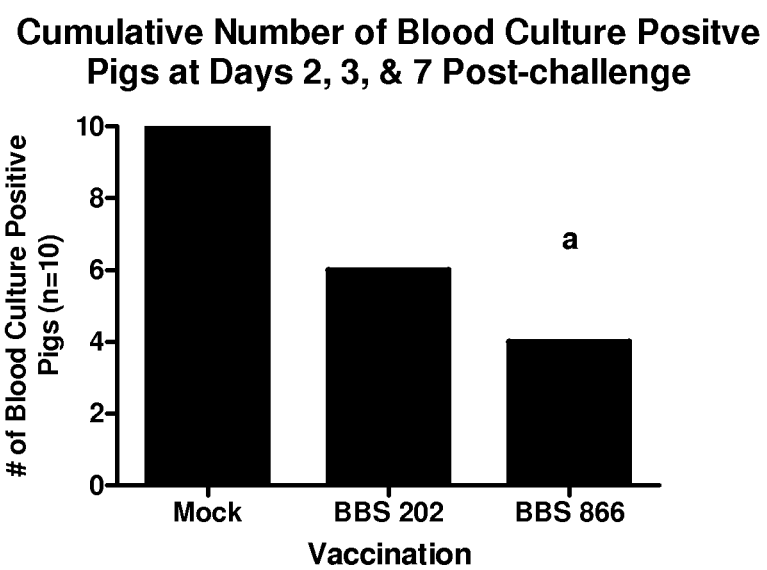
FIG. 3C shows the total number of pigs in each group that are blood culture-positive for S. Choleraesuis at any sample time (days 2, 3, and 7) post-challenge.

As indicated in the Table 2, supra, many different novel, mutated *S. enterica* serovar Typhimurium are generated, including bacteria with null mutations in one or more of the following genes: rybB, omrA, omrB, micA, and invR. Further, bacteria are generated containing an LPS production mutation (null mutation in rfaH) in combination with null mutations in one or more of the following genes: rybB, omrA, omrB, micA, and invR. Some of the bacteria described in Table 2 possess the kanamycin resistance gene and/or nalidixic acid resistance gene. Bacteria containing the same mutations in LPS production mutation (null mutation in rfaH) in combination with null mutations in one or more of rybB, omrA, omrB, micA, and invR, but lacking the kanamycin resistance gene are generated. The *S. enterica* serovar Typhimurium strain BBS 1134 is a derivative of strain BBS 866 with a deletion of the neo gene inserted in rfaH. Thus, with only a deletion of the neo gene, one of ordinary skill in the art would expect that strain BBS 1134 has the same efficacy as strain BBS 866 in swine, turkey and other animals.

Example 2

Live, Attenuated Mutants of *S. enterica* Serovar Typhimurium Cross-Protect Swine Against *S. enterica* Serovar Choleraesuis Infections At three-weeks of age, piglets receive intranasal administration of 1 ml of PBS (mock-vaccinated) or PBS containing $1.0\times10^9$ cfu of live attenuated *S. enterica* serovar Typhimurium strains BBS 202 (rfaH::neo, single mutant, vaccinated) or BBS 866 (ΔrybB ΔomrAB ΔmicA ΔinvR rfaH::neo, quintuple mutant, vaccination). The rectal temperature is monitored at 0, 1, 2, 3, and 7 days following vaccination. As shown in FIG. 1, vaccination of swine with either BBS 202 or BBS 866 mutants does not induce a significant increase in the swine rectal temperature compared to mock-vaccinated swine. In FIG. 1, "a" indicates significance compared to mock-vaccinated swine.

At seven-weeks of age all pigs are intranasally challenged with 1 ml of PBS containing $1\times10^9$ cfu of wild-type *S. enterica* serovar Choleraesuis. The rectal temperature is monitored at 0, 1, 2, 3, and 7 days following challenge. As seen in FIG. 2, a significant increase in the rectal temperature is observed for both mock-vaccinated (P=0.0002) and the BBS 202 vaccinated (P=0.0123) swine at day 1 post-challenge compared to day 0; a significant increase in rectal temperature is not observed in the BBS 866 vaccinated pigs. In FIG. 2, "a" indicates significance compared to mock-vaccinated swine, and "b" indicates significance compared to BBS 202 vaccinated swine A significantly lower swine rectal temperature is seen at day 1 post-challenge for the BBS 866 vaccinated swine compared to both mock-vaccinated (P<0.01) and the BBS 202 vaccinated (P<0.05) swine. At day 3 post-challenge, the swine rectal temperature is significantly reduced in the BBS 866 vaccinated swine compared to the mock-vaccinated (P<0.05) swine. At 7 days post-challenge, a significantly lower swine rectal temperature is observed for both the BBS 202 (P<0.001) and BBS 866 (P<0.001) vaccinated pigs compared to the mock-vaccinated swine. Furthermore, a significant increase in the rectal temperature is observed for mock-vaccinated swine (P<0.0001) at day 7 post-challenge compared to day 0; however, a significant increase is not observed in either the BBS 202 vaccinated or the BBS 866 vaccinated pigs for this comparison.

Following vaccination with either BBS 202 or BBS 866 and then challenged, blood cultures are negative for *S. enterica* serovar Choleraesuis at day 1 but culture-positive at days 2, 3, and 7 post-inoculation for a subset of pigs. The blood culture results are analyzed in several ways including: a) the cumulative number of positive blood cultures over several days, b) the number of positive blood cultures at 7 days post-inoculation, and c) the cumulative number of blood culture-positive pigs over time. Cumulative blood culture results for days 2, 3, and 7 post-challenge indicate a significantly higher quantity (24 vs 11 and 7, respectively) of positive-blood cultures comparing mock-vaccinated to both the BBS 202 (P=0.0014) and BBS 866 (P<0.0001) vaccinated pigs. See FIG. 3A, where "a" indicates significance compared to mock-vaccinated swine. Analysis of blood culture results at the termination of the vaccine trial (7 days post-challenge) indicates that both the BBS 202 vaccinated swine (P=0.0198) and the BBS 866 vaccinated pigs (P=0.0055) have a significantly lower quantity (3 and 2 vs. 9, respectively) of positive-blood cultures compared to mock-vaccinated pigs. See FIG. 3B, where "a" indicates significance compared to mock-vaccinated swine. Analysis of the number of pigs in each group that are blood culture-positive at any time indicates that the cumulative number of blood culture positive pigs is significantly different comparing mock-vaccinated to BBS 866 (P=0.0108) vaccinated pigs. At days 2, 3, or 7 post-challenge, a total of four pigs are culture-positive in the BBS 866 vaccinated group but all ten swine in the mock-vaccinated group are positive a minimum of at least one day. See FIG. 3C where "a" indicates significance compared to mock-vaccinated swine.

Figure 4:
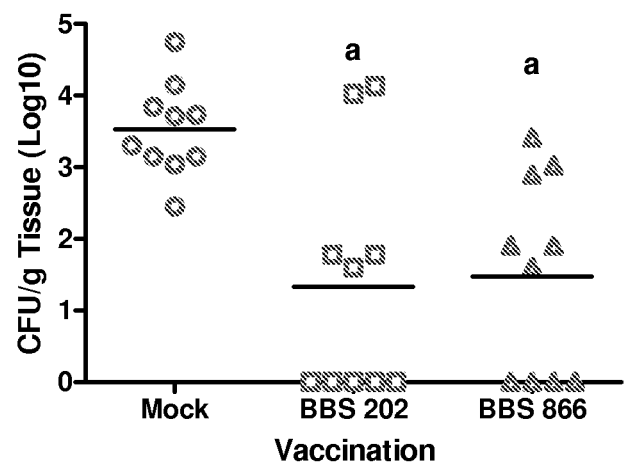
FIG. 4 shows the number of colony forming units (cfu) of *S. enterica* serovar Choleraesuis per gram of liver tissue at seven days post-challenge of swine immunized with either *S. enterica* serovar Typhimurium mutant strain BBS 202 or mutant strain BBS 866 or PBS buffer (mock immunized).

At day 7 post-challenge the *S. enterica* serovar Choleraesuis cfu/g of liver tissue is significantly lower in both the BBS 202 (P=0.0051) and the BBS 866 (P=0.0023) vaccinated pigs compared to mock-vaccinated pigs. See FIG. 4 where "a" indicates significance compared to mock-vaccinated swine.

Figure 5A:
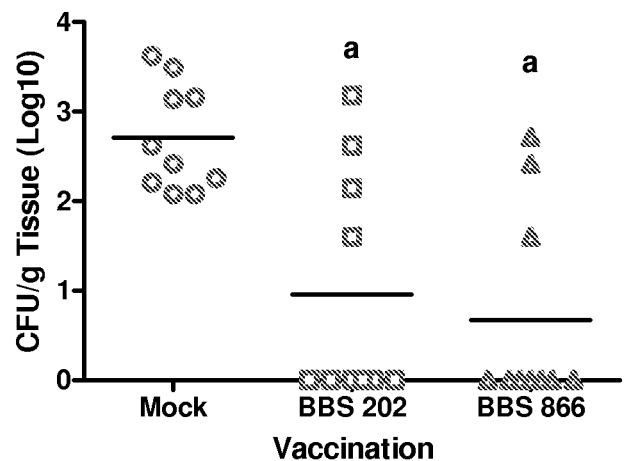
FIG. 5A shows the cfu of *S. enterica* serovar Choleraesuis per gram of spleen tissue at seven days post-challenge of swine immunized with either *S. enterica* serovar Typhimurium mutant strain BBS 202 or mutant strain BBS 866 or PBS buffer (mock immunized).
Figure 5B:
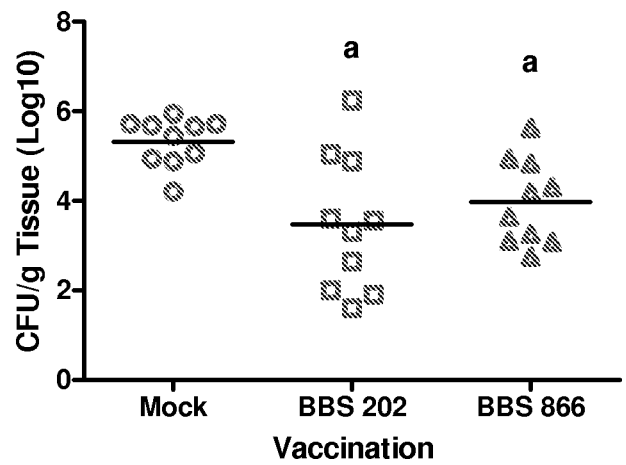
FIG. 5B shows the cfu of *S. enterica* serovar Choleraesuis per gram of Peyer's Patch tissue at seven days post-challenge of swine immunized with either *S. enterica* serovar Typhimurium mutant strain BBS 202 or mutant strain BBS 866 or PBS buffer (mock immunized).
Figure 5C:
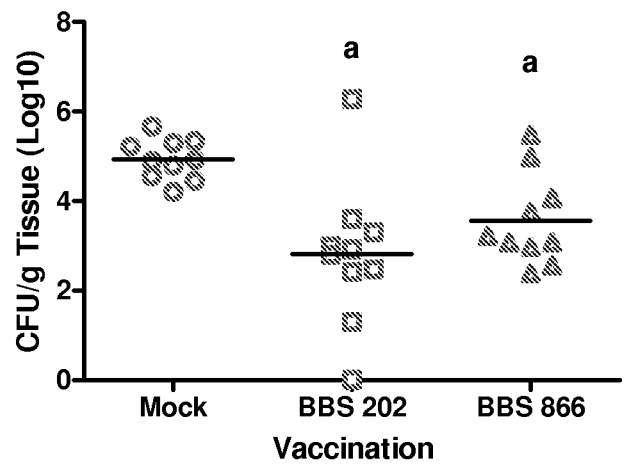
FIG. 5C shows the cfu of *S. enterica* serovar Choleraesuis per gram of ileocecal lymph node (ICLN) tissue at seven days post-challenge of swine immunized with either *S. enterica* serovar Typhimurium mutant strain BBS 202 or mutant strain BBS 866 or PBS buffer (mock immunized).
Figure 5D:
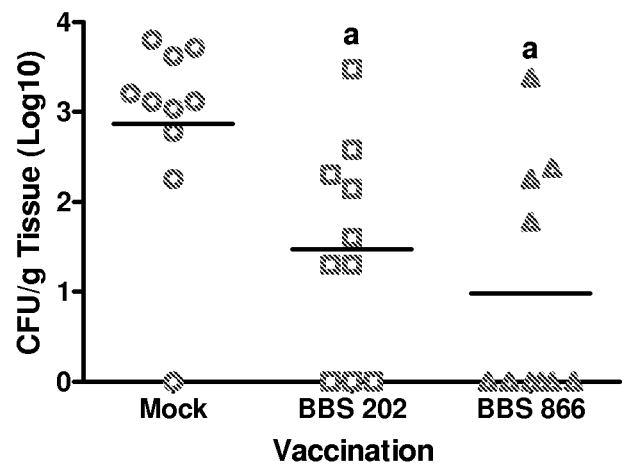
FIG. 5D shows the cfu of *S. enterica* serovar Choleraesuis per gram of tonsular tissue at seven days post-challenge of swine immunized with either *S. enterica* serovar Typhimurium mutant strain BBS 202 or mutant strain BBS 866 or PBS buffer (mock immunized).

At day 7 post-challenge the *S. enterica* serovar Choleraesuis cfu/g of spleen tissue is significantly lower in both the BBS 202 (P=0.0030) and BBS 866 (P=0.0015) vaccinated swine compared to mock-vaccinated pigs. See FIG. 5A where "a" indicates significance compared to mock-vaccinated swine. At day 7 post-challenge the *S. enterica* serovar Choleraesuis cfu/g of Peyer's Patch tissue is significantly lower in both the BBS 202 (P=0.0093) and BBS 866 (P=0.0041) vaccinated pigs compared to mock-vaccinated pigs. See FIG. 5B where "a" indicates significance compared to mock-vaccinated swine. At day 7 post-challenge the *S. enterica* serovar Choleraesuis cfu/g of ileocecal lymph node (ICLN) tissue is significantly lower in both the BBS 202 (P=0.0045) and BBS 866 (P=0.0021) vaccinated pigs compared to mock-vaccinated swine. See FIG. 5C where "a" indicates significance compared to mock-vaccinated swine. At day 7 post-challenge the *S. enterica* serovar Choleraesuis cfu/g of tonsil tissue is significantly lower in both the BBS 202 (P=0.0390) and BBS 866 (P=0.0060) vaccinated swine compared to mock-vaccinated pigs. See FIG. 5D where "a" indicates significance compared to mock-vaccinated swine.

Figure 6A:
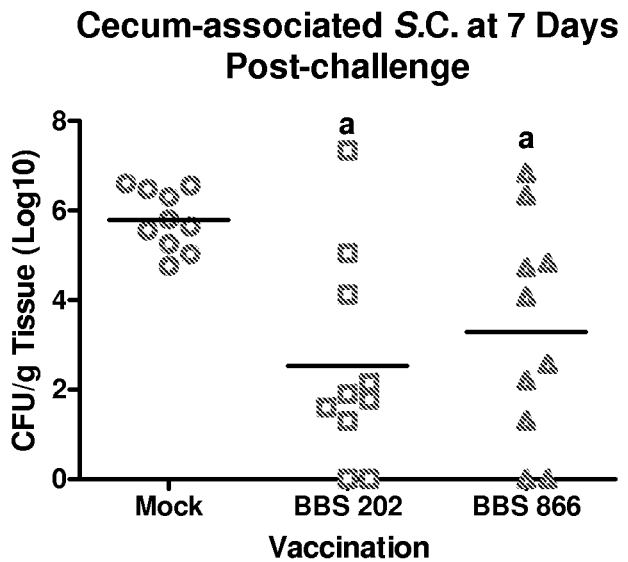
FIG. 6A shows the cfu of *S. enterica* serovar Choleraesuis per gram of cecum tissue at seven days post-challenge of swine immunized with either *S. enterica* serovar Typhimurium mutant strain BBS 202 or mutant strain BBS 866 or PBS buffer (mock immunized).
Figure 6B:
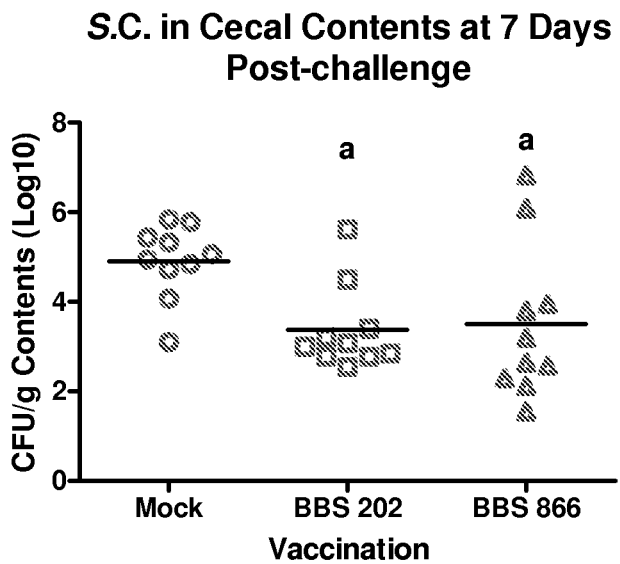
FIG. 6B shows the cfu of *S. enterica* serovar Choleraesuis per gram of cecum content at seven days post-challenge of swine immunized with either *S. enterica* serovar Typhimurium mutant strain BBS 202 or mutant strain BBS 866 or PBS buffer (mock immunized).

At day 7 post-challenge, the *S. enterica* serovar Choleraesuis cfu/g in cecum tissue is significantly lower in both the BBS 202 (P=0.0028) and BBS 866 (P=0.0129) vaccinated pigs compared to mock-vaccinated pigs. See FIG. 6A where "a" indicates significance compared to mock-vaccinated swine. At day 7 post-inoculation the *S. enterica* serovar Choleraesuis cfu/g of cecal contents is significantly lower in both the BBS 202 (P=0.0042) and BBS 866 (P=0.0274) vaccinated swine compared to mock-vaccinated pigs. See FIG. 6B where "a" indicates significance compared to mock-vaccinated swine.

Figure 7:
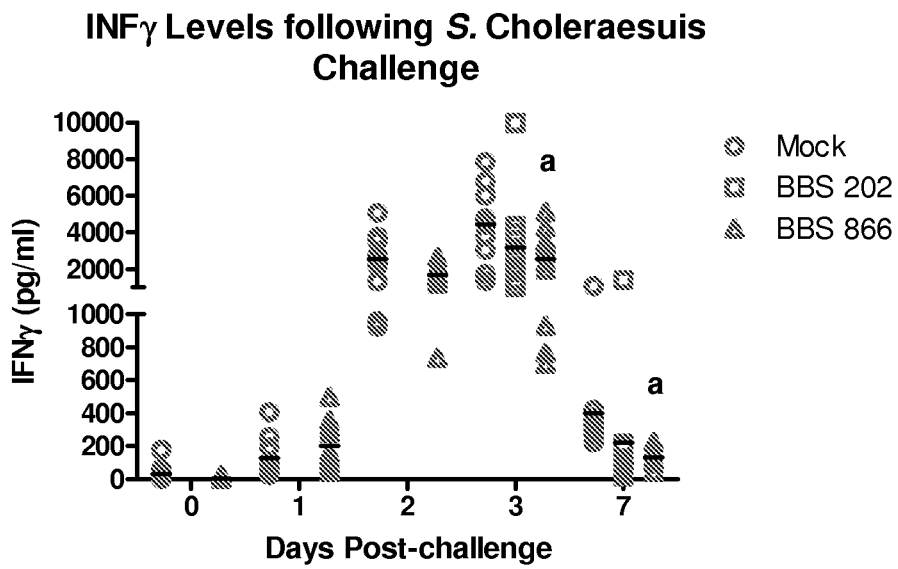
FIG. 7 shows the interferon-γ levels in serum of swine immunized with either *S. enterica* serovar Typhimurium mutant strain BBS 202 or mutant strain BBS 866 or PBS buffer (mock immunized) at 0, 1, 2, 3, and 7 days post-challenge with *S. enterica* serovar Choleraesuis.

A Th1 immune response is generated against viral and intracellular bacterial pathogens and is characterized by production of the cytokine interferon-gamma (IFNγ). Analysis of serum IFNγ levels in *S. enterica* serovar Choleraesuis challenged swine indicates a significantly lower IFNγ level in the BBS 866 vaccinated pigs compared to mock-vaccinated swine at days 3 and 7 post-inoculation (P=0.0345 and P=0.0035, respectively). See FIG. 7 where "a" indicates significance compared to mock-vaccinated swine.

Example 3

Figure 8:
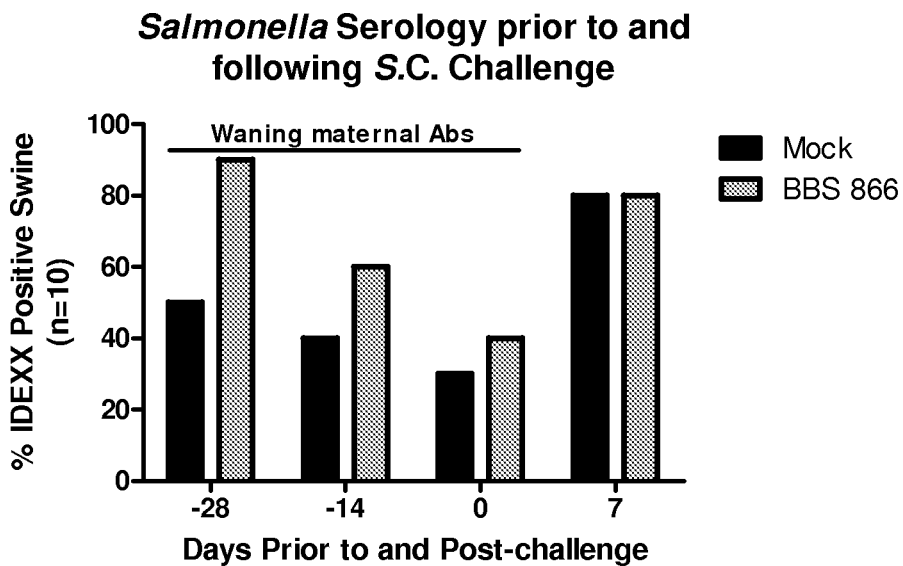
FIG. 8 compares the percentage of swine positive for antibodies to *Salmonella* LPS at 14 and 28 (day of vaccination) days prior to challenge, at challenge (0), and seven days post-challenge (with *S. enterica* serovar Choleraesuis) for swine vaccinated with strain BBS 866 or PBS buffer (mock immunized).

Live, Attenuated *S. enterica* Serovar Typhimurium Mutants Reduce Carriage in Swine and are a DIVA Vaccine Piglets for the BBS 866 vaccine trial with *S. enterica* serovar Choleraesuis challenge are the offspring from four sows. These sows are screened prior to farrowing, and it is determined that they are not shedding *Salmonella* in their feces. However, serological analysis of sow serum using the IDEXX Swine *Salmonella* Ab Test (Westbrook, Me.) indicates that 3 of the 4 sows are positive for antibodies to *Salmonella* LPS. Upon screening at three-weeks of age, a subset of piglets (from the three *Salmonella*-antibody-positive sows) in both the BBS 866-vaccinated and mock-vaccinated groups are positive for antibodies to *Salmonella* LPS. This screening corresponds to the day of initial BBS 866 vaccination and mock vaccination (28 days prior to challenge). Over a 4-week period, the number of pigs with serum containing antibodies to *Salmonella* LPS decline in both BBS 866-vaccinated and mock-vaccinated pigs. These results suggest that the initial detection of antibodies to *Salmonella* LPS in piglet serum is caused by maternal antibodies that wane until the day of *S. enterica* serovar Choleraesuis challenge. Furthermore, vaccination of pigs with BBS 866 (−28 days prior to challenge) does not induce an antibody response against LPS derived from *Salmonella* serogroups B (includes *S. enterica* serovar Typhimurium), C1 (includes *S. enterica* serovar Choleraesuis), and D present in the IDEXX Swine *Salmonella* Ab Test. This methodology is utilized especially in Europe to screen swine herds for the prevalence of the most common *Salmonella* spp. Thus, vaccination with BBS 866 does not interfere with the monitoring for herd level prevalence of *Salmonella* spp. Based on these results, the BBS 866 vaccine strain is a DIVA (Differentiation of Infected from Vaccinated Animals) that can be used to induce immune cross-protection to reduce disease severity caused by *Salmonella* spp. At day 7 post-challenge with wild-type *S. enterica* serovar Choleraesuis, serum from 80% of BBS 866-vaccinated and 80% of mock-vaccinated pigs are positive in the IDEXX Swine *Salmonella* Ab Test. These results demonstrate that greater than one-half of the pigs without maternal antibodies to *Salmonella* LPS are able to induce an immune response to the LPS antigen(s) present on *S. enterica* serovar Choleraesuis following challenge. See FIG. 8.

Example 4

Figure 9:
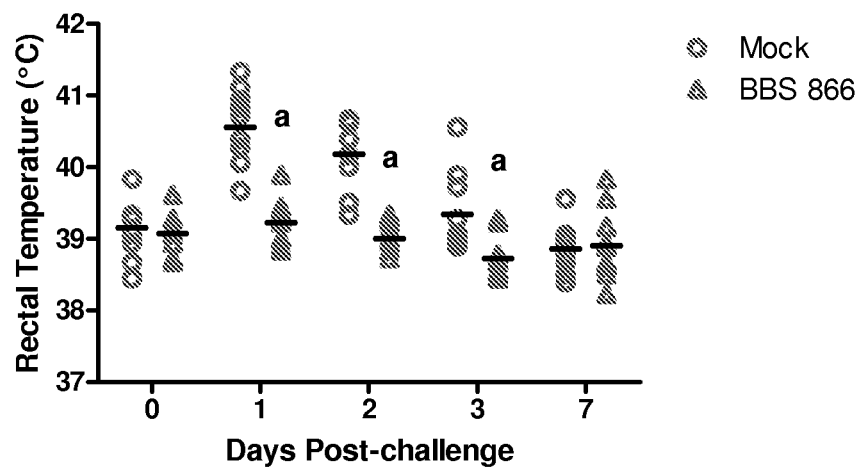
FIG. 9 illustrates the rectal temperature of piglets vaccinated with strain BBS 866 or PBS buffer (mock immunized) at 0, 1, 2, 3, and 7 days after challenge with *S. enterica* serovar Typhimurium.

Live, Attenuated *S. enterica* Serovar Typhimurium Mutants Protect Swine Against Wild-Type *S. enterica* Serovar Typhimurium Infections and Reduce Colonization At four-weeks of age, piglets receive an intranasal administration of 1 ml of PBS (mock-vaccinated) or PBS containing $1.0 \times 10^{10}$ cfu of a live attenuated *S. enterica* serovar Typhimurium strain BBS 866 (ΔrybB ΔomrAB ΔmicA ΔinvR rfaH::neo, quintuple mutant, vaccination). Two weeks later, piglets receive a booster of either PBS or PBS containing $4.0 \times 10^9$ cfu of BBS 866. At nine-weeks of age, all pigs are intranasally challenged with 1 ml of PBS containing $2 \times 10^8$ cfu of SB 377, a virulent *S. enterica* serovar Typhimurium UK1 strain (previously inoculated into a pig and re-isolated from the ileocecal lymph node 7 days after challenge). The rectal temperature is monitored at 0, 1, 2, 3, and 7 days following challenge. As seen in FIG. 9, a significantly lower swine rectal temperature is seen at days 1, 2, and 3 post-challenge for the BBS 866 vaccinated swine compared to mock-vaccinated swine (P<0.0001, P<0.0001, and P=0.0057, respectively).

Figure 10:
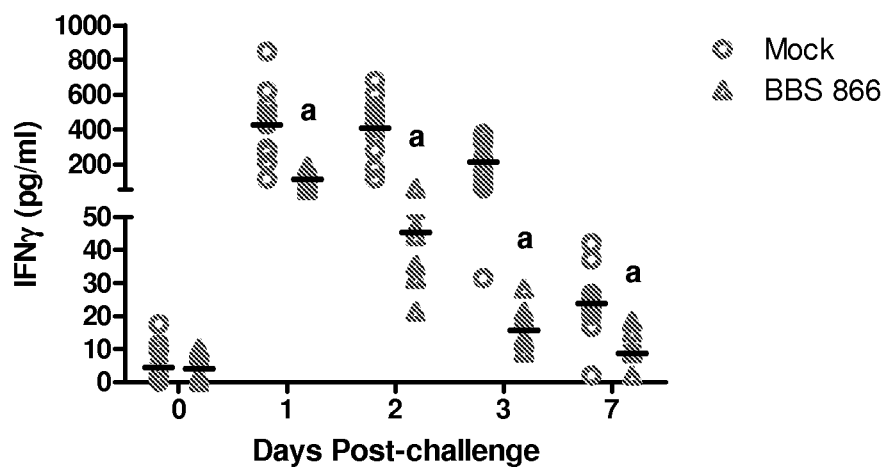
FIG. 10 illustrates interferon γ levels in plasma of piglets vaccinated with strain BBS 866 or PBS buffer (mock immunized) at 0, 1, 2, 3, and 7 days after challenge with *S. enterica* serovar Typhimurium.

As seen in FIG. 10, analysis of plasma IFNγ levels in S. enterica serovar Typhimurium challenged swine indicates a significantly lower IFN' level in the BBS 866 vaccinated pigs compared to mock-vaccinated swine at days 1, 2, 3, and 7 post-challenge (P=0.0003, P<0.0001, P=0.0002, and P=0.0017, respectively) (where "a" indicates significant difference between mock vaccinated and BBS 866 vaccinated pigs).

Figure 11:
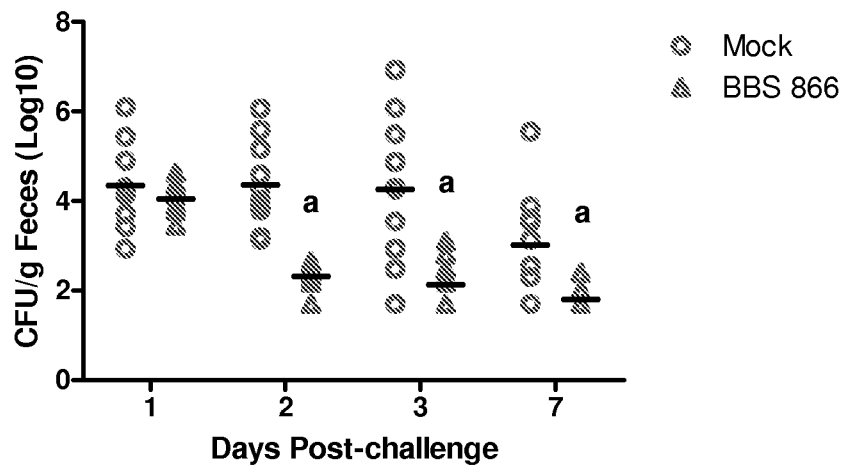
FIG. 11 illustrates fecal shedding of piglets vaccinated with strain BBS 866 or PBS buffer (mock immunized) at 1, 2, 3, and 7 days after challenge with *S. enterica* serovar Typhimurium.

Fecal shedding of S. enterica serovar Typhimurium is significantly lower at days 2, 3, and 7 post-challenge in BBS 866 vaccinated pigs compared to mock-vaccinated swine (P<0.0001, P=0.0011, and P=0.0047, respectively). See FIG. 11 where "a" indicates significant difference between mock vaccinated and BBS 866 vaccinated pigs. At day 7 post-challenge, fecal samples from 7 of 10 pigs vaccinated with BBS 866 are below the quantifiable level of detection for S. enterica serovar Typhimurium (but enrichment positive) compared with only 2 of 10 samples from mock-vaccinated pigs (P=0.0349).

Figure 12:
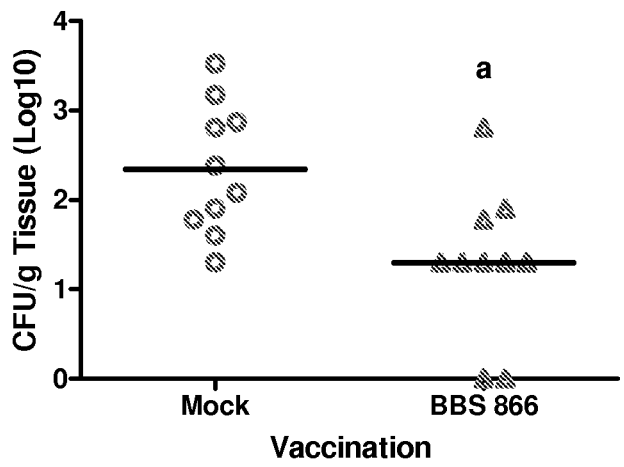
FIG. 12 shows Peyer's Patch-associated *S. enterica* serovar Typhimurium cfu/g in piglets vaccinated with strain BBS 866 or PBS buffer (mock immunized) at 7 days after challenge with *S. enterica* serovar Typhimurium.

At day 7 post-challenge, the S. enterica serovar Typhimurium cfu/g of Peyer's Patch tissue is significantly lower in BBS 866 vaccinated pigs compared to mock-vaccinated pigs (P=0.0081). See FIG. 12, where "a" indicates significant difference between mock vaccinated and BBS 866 vaccinated pigs. Furthermore, Peyer's Patch tissues from 7 of 10 pigs vaccinated with BBS 866 are below the quantifiable level of detection for S. enterica serovar Typhimurium (2 enrichment negative and 5 enrichment positive) compared with all 10 samples of the mock-vaccinated pigs that are quantifiable (P=0.0015).

Figure 13:
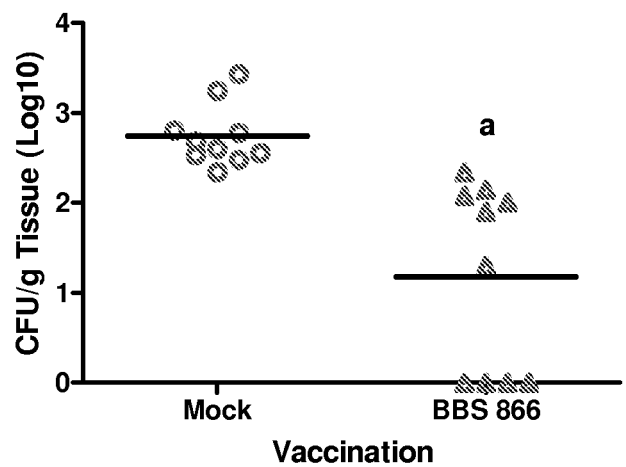
FIG. 13 shows ileocecal lymph node-associated *S. enterica* serovar Typhimurium cfu/g in piglets vaccinated with strain BBS 866 or PBS buffer (mock immunized) at 7 days after challenge with *S. enterica* serovar Typhimurium.

At day 7 post-challenge, the S. enterica serovar Typhimurium cfu/g of ileocecal lymph node (ICLN) tissue is significantly lower in BBS 866 vaccinated pigs compared to mock-vaccinated swine (P=0.0003). See FIG. 13, where "a" indicates significant difference between mock vaccinated and BBS 866 vaccinated pigs. Furthermore, ICLN tissues from 4 of 10 pigs vaccinated with BBS 866 are negative for S. enterica serovar Typhimurium compared to all 10 samples of the mock-vaccinated pigs that are quantifiable (P=0.0433).

Figure 14:
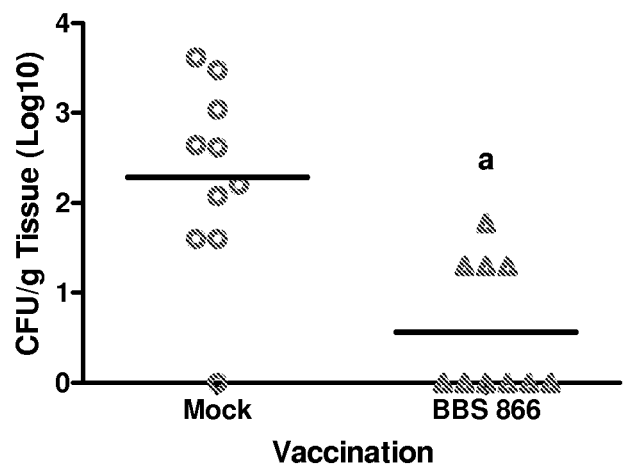
FIG. 14 shows cecum-associated *S. enterica* serovar Typhimurium cfu/g in piglets vaccinated with strain BBS 866 or PBS buffer (mock immunized) at 7 days after challenge with *S. enterica* serovar Typhimurium.
Figure 15:
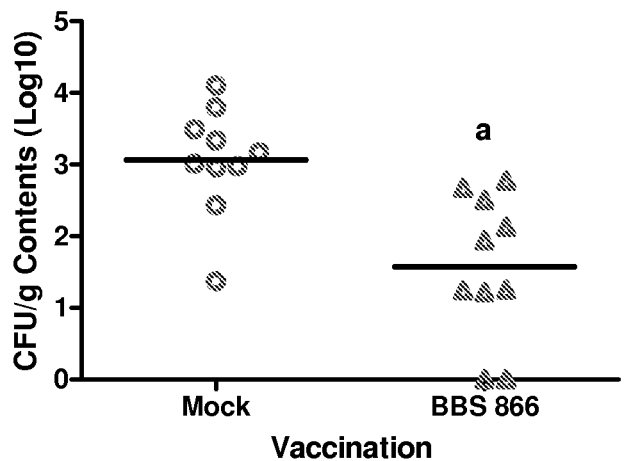
FIG. 15 shows *S. enterica* serovar Typhimurium cfu/g obtained from cecum contents in piglets vaccinated with strain BBS 866 or PBS buffer (mock immunized) at 7 days after challenge with *S. enterica* serovar Typhimurium.

At day 7 post-challenge, the S. enterica serovar Typhimurium cfu/g in cecum tissue is significantly lower in BBS 866 vaccinated pigs compared to mock-vaccinated pigs (P=0.0006). See FIG. 14, where "a" indicates significant difference between mock vaccinated and BBS 866 vaccinated pigs. Furthermore, cecum tissues from 6 of 10 pigs vaccinated with BBS 866 are negative for S. enterica serovar Typhimurium compared with only 1 of 10 samples from mock-vaccinated pigs (P=0.0286). At day 7 post-challenge, the S. enterica serovar Typhimurium cfu/g of cecal contents is significantly lower in BBS 866 vaccinated swine compared to mock-vaccinated pigs (P=0.0016). See FIG. 15, where "a" indicates significant difference between mock vaccinated and BBS 866 vaccinated pigs.

Figure 16:
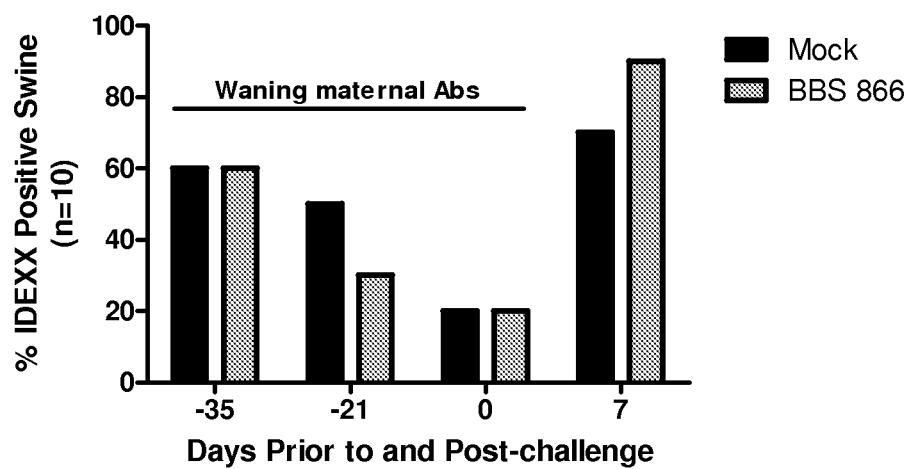
FIG. 16 compares the percentage of swine positive for antibodies to *Salmonella* LPS at 21 (day of booster vaccination) and 35 (day of vaccination) days prior to challenge, at challenge (0), and seven days post-challenge (with *S. enterica* serovar Typhimurium) for swine vaccinated with strain BBS 866 or PBS buffer (mock immunized).

Piglets for the BBS 866 vaccine trial with S. enterica serovar Typhimurium challenge are the offspring from four sows. These sows are screened prior to farrowing and are determined to not be shedding Salmonella in their feces. However, serological analysis of sow serum using the IDEXX Swine Salmonella Ab Test (Westbrook, Me.) indicates that 3 of the 4 sows are positive for antibodies to Salmonella LPS. Upon screening at four-weeks of age (day of vaccination), a subset of piglets (from the three Salmonella-antibody-positive sows) are positive for antibodies to Salmonella LPS. This screening corresponds to the day of initial BBS 866 vaccination and mock vaccination. Over a 5-week period, the number of pigs with plasma containing antibodies to Salmonella LPS declines in both BBS 866-vaccinated and mock-vaccinated pigs. These results suggest that the initial detection of antibodies to Salmonella LPS in piglet plasma is caused by maternal antibodies that wane until the day of S. enterica serovar Typhimurium challenge. Furthermore, vaccination of pigs with 2 doses of BBS 866 (at −35 and −21 days prior to challenge) does not induce an antibody response against LPS derived from Salmonella serogroups B (includes S. enterica serovar Typhimurium), C1, and D present in the IDEXX Swine Salmonella Ab Test. As discussed above, this methodology is utilized especially in Europe to screen swine herds for the prevalence of the most common Salmonella spp. Thus, vaccination with BBS 866 does not interfere with the monitoring for herd level prevalence of Salmonella spp. Based on these results, the BBS 866 vaccine strain is a DIVA (Differentiation of Infected from Vaccinated Animals) and can be used to reduce gastrointestinal colonization, pathogen fecal shedding and disease severity caused by Salmonella spp. At day 7 post-challenge with wild-type S. enterica serovar Typhimurium (SB 377), plasma from 90% of BBS 866-vaccinated and 70% of mock-vaccinated pigs are positive in the IDEXX Swine Salmonella Ab Test (see FIG. 16). These results demonstrate that most of the pigs do not have antibodies to Salmonella LPS just prior to challenge, but most of the pigs are able to induce an immune response to the LPS antigen(s) present on the virulent S. enterica serovar Typhimurium strain following challenge.

Example 5

Live, Attenuated S. enterica Serovar Typhimurium Mutants Protect Turkeys Against S. enterica Serovar Typhimurium Challenge At two-days of age, turkey poults receive an oral gavage of 500 µl of PBS (mock-vaccinated) or PBS containing $4 \times 10^8$ cfu of the live, attenuated S. enterica serovar Typhimurium strain BBS 866. At 2-weeks of age, poults receive a 1 ml booster of either PBS or PBS containing $1 \times 10^9$ cfu of BBS 866. At 5-weeks of age all turkeys are challenged via oral gavage with $5 \times 10^9$ cfu of SB 391, a wild-type S. enterica serovar Typhimurium UK1 strain (previously inoculated into a turkey and re-isolated from the ceca 7 days after challenge). Seven days after challenge, necropsies are performed on both mock-vaccinated and BBS 866 vaccinated turkeys that had been challenged with S. enterica serovar Typhimurium UK1, and their spleen and cloaca are harvested for examination.

Figure 17:
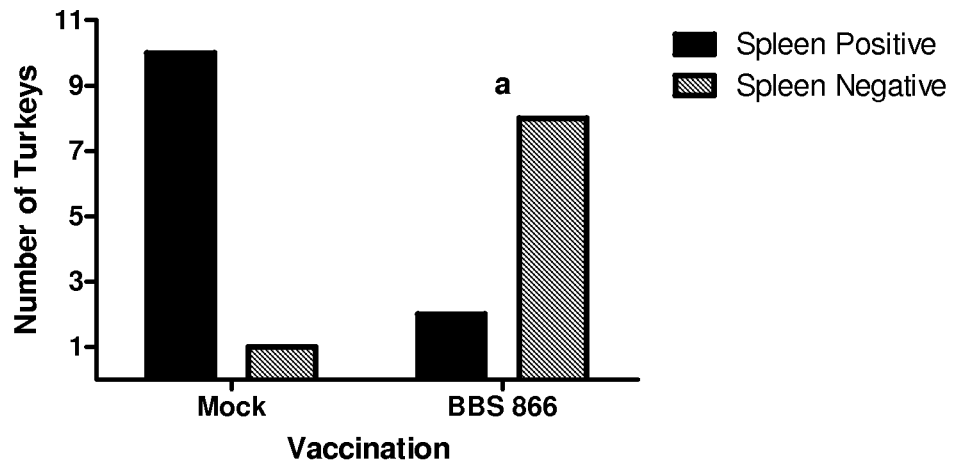
FIG. 17 illustrates the number of turkeys vaccinated with either strain BBS 866 or PBS buffer (mock immunized) from whose spleen *S. enterica* serovar Typhimurium are isolated seven days post-challenge with *S. enterica* serovar Typhimurium (spleen positive) or from whose spleen no *S. enterica* serovar Typhimurium are isolated seven days post-challenge with *S. enterica* serovar Typhimurium (spleen negative).
Figure 18:
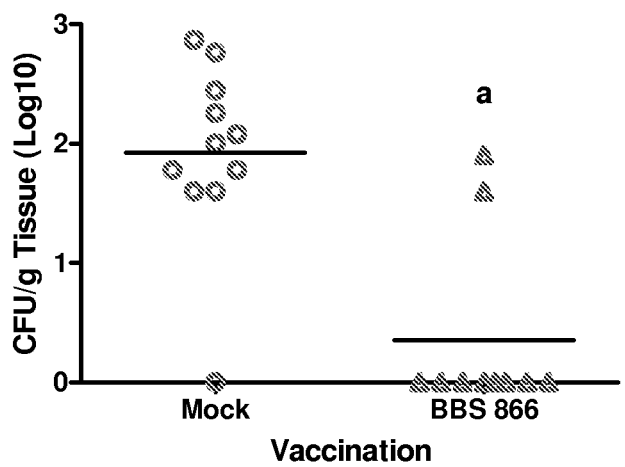
FIG. 18 shows *S. enterica* serovar Typhimurium cfu/g obtained from spleens in turkeys vaccinated with strain BBS 866 or PBS buffer (mock immunized) at 7 days after challenge with *S. enterica* serovar Typhimurium.
Figure 19:
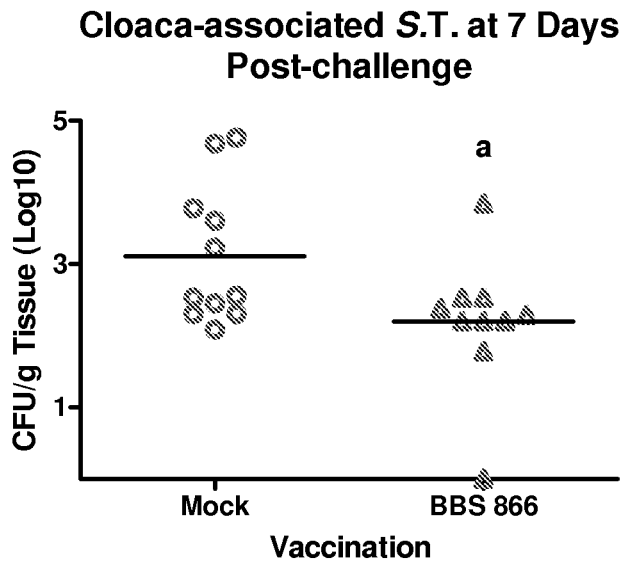
FIG. 19 shows *S. enterica* serovar Typhimurium cfu/g obtained from cloaca in turkeys vaccinated with strain BBS 866 or PBS buffer (mock immunized) at 7 days after challenge with *S. enterica* serovar Typhimurium.

Bacterial isolation of Salmonella from spleen tissue indicates systemic infection. At day 7 post-challenge with S. enterica serovar Typhimurium UK1, the number of turkeys that are positive for S. enterica serovar Typhimurium isolation from the spleen is significantly lower in BBS 866 vaccinated turkeys compared to mock-vaccinated turkeys (P=0.0019). See FIG. 17 where "a" indicates significance compared to mock-vaccinated turkeys. At day 7 post-challenge the S. enterica serovar Typhimurium cfu/g of spleen tissue is significantly decreased in BBS 866 vaccinated turkeys compared to mock-vaccinated turkeys (P=0.0001). See FIG. 18 where "a" indicates significance compared to mock-vaccinated turkeys. Bacterial isolation of *Salmonella* from cloaca tissue indicates gastrointestinal colonization. At day 7 post-challenge, the *S. enterica* serovar Typhimurium cfu/g of cloaca tissue is significantly lower in BBS 866 vaccinated turkeys compared to mock-vaccinated turkeys (P=0.0404). See FIG. 19 where "a" indicates significance compared to mock-vaccinated turkeys. This data demonstrates that BBS 866 protects turkeys from systemic infection and gastrointestinal colonization by *S. enterica* serovar Typhimurium that infects turkeys.

Example 6

Live, Attenuated *S. enterica* Serovar Typhimurium Mutants Cross-Protect Turkeys Against *S. enterica* Serovar Heidelberg Challenge At two-days of age, turkey poults receive an oral gavage of 500 µl of PBS (mock-vaccinated) or PBS containing $4 \times 10^8$ cfu of the live attenuated *S. enterica* serovar Typhimurium strain BBS 866. At 2-weeks of age, poults receive a 1 ml booster of either PBS or PBS containing $1 \times 10^9$ cfu of BBS 866. At 5-weeks of age all turkeys are challenged via oral gavage with $1 \times 10^9$ cfu of SB 392, a multidrug-resistant *S. enterica* serovar Heidelberg strain (previously inoculated into a turkey and re-isolated from the ceca 7 days after challenge). Seven days after challenge, necropsies are performed on both mock-vaccinated and BBS 866 vaccinated turkeys that had been challenged with *S. enterica* serovar Heidelberg, and their spleen and ceca are harvested for examination.

Figure 20:
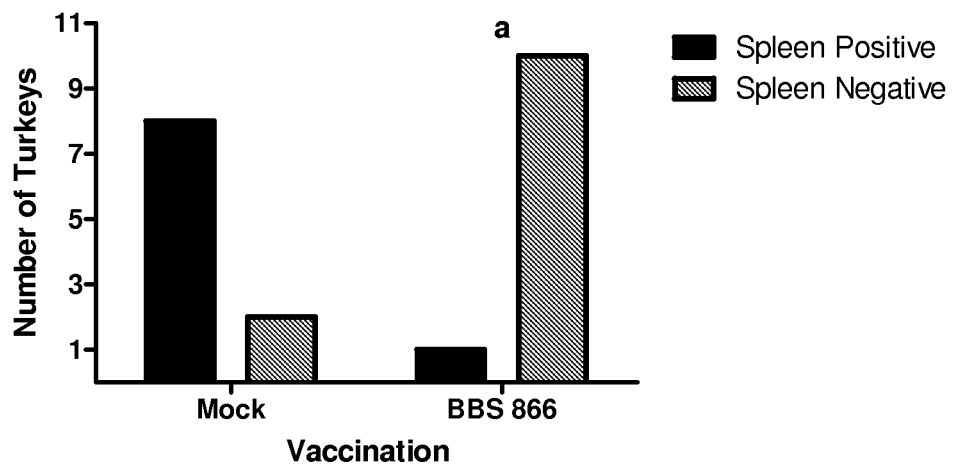
FIG. 20 illustrates the number of turkeys vaccinated with either strain BBS 866 or PBS buffer (mock immunized) from whose spleen *S. enterica* serovar Heidelberg are isolated seven days post-challenge with *S. enterica* serovar Heidelberg (spleen positive) or from whose spleen no *S. enterica* serovar Heidelberg are isolated seven days post-challenge with *S. enterica* serovar Heidelberg (spleen negative).
Figure 21:
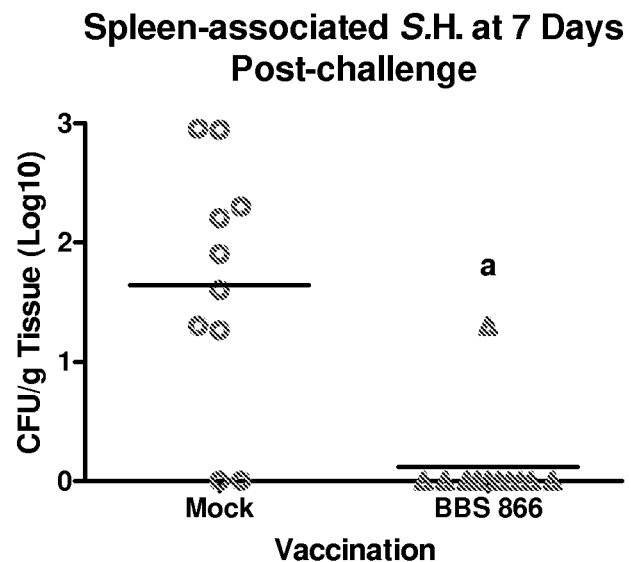
FIG. 21 shows *S. enterica* serovar Heidelberg cfu/g obtained from spleens in turkeys vaccinated with strain BBS 866 or PBS buffer (mock immunized) at 7 days after challenge with *S. enterica* serovar Heidelberg.
Figure 22:
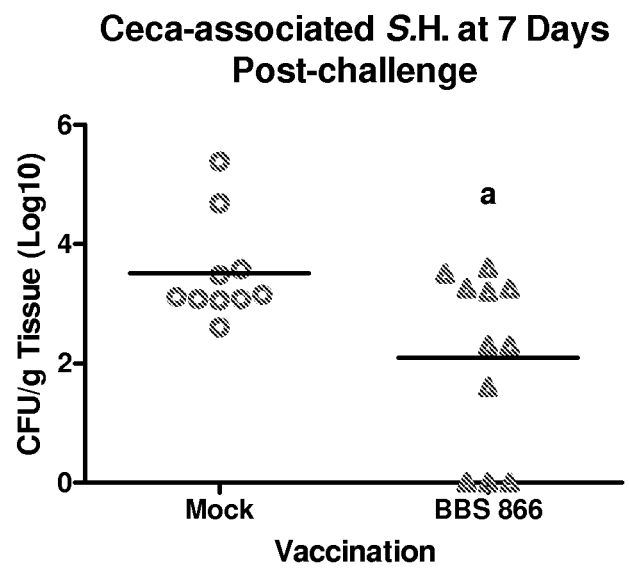
FIG. 22 shows *S. enterica* serovar Heidelberg cfu/g obtained from ceca in turkeys vaccinated with strain BBS 866 or PBS buffer (mock immunized) at 7 days after challenge with *S. enterica* serovar Heidelberg.

Bacterial isolation of *Salmonella* from spleen tissue indicates systemic infection. At day 7 post-challenge with *S. enterica* serovar Heidelberg, the number of turkeys that are positive for *S. enterica* serovar Heidelberg isolation from the spleen is significantly lower in BBS 866 vaccinated turkeys compared to mock-vaccinated turkeys (P=0.0019). See FIG. 20 where "a" indicates significance compared to mock-vaccinated turkeys. At day 7 post-challenge, the *S. enterica* serovar Heidelberg cfu/g of spleen tissue is significantly decreased in BBS 866 vaccinated turkeys compared to mock-vaccinated turkeys (P=0.0002). See FIG. 21 where "a" indicates significance compared to mock-vaccinated turkeys. Bacterial isolation of *Salmonella* from ceca tissue indicates gastrointestinal colonization. At day 7 post-challenge, the *S. enterica* serovar Heidelberg cfu/g of ceca tissue is significantly lower in BBS 866 vaccinated turkeys compared to mock-vaccinated turkeys (P=0.0149). See FIG. 22 where "a" indicates significance compared to mock-vaccinated turkeys. This data demonstrates that BBS 866 generates cross-protection in turkeys from systemic infection and gastrointestinal colonization by *S. enterica* serovar Heidelberg.

The terms "approximately" and "about" refers to a quantity, level, value or amount that varies by as much as 30%, or in another embodiment by as much as 20%, and in a third embodiment by as much as 10% to a reference quantity, level, value or amount. As used herein, the singular form "a", "an", and "the" include plural references unless the context clearly dictates otherwise. For example, the term "a bacterium" includes both a single bacterium and a plurality of bacteria.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation. All documents cited herein are incorporated by reference.

We the inventors claim:

1. A mutated S. enterica serovar Typhimurium comprising a null mutation in invR, micA, rybB, rfaH, omrA and omrB genes.

2. The mutated S. enterica serovar Typhimurium of claim 1, wherein said S. enterica serovar Typhimurium is strain BBS 866 deposited under the accession NRRL B-50989 or strain BBS 1134 deposited under the accession NRRL B-50990.

3. An immunogenic composition comprising a pharmaceutically acceptable carrier or diluent and a mutated S. enterica serovar Typhimurium comprising a null mutation in invR, micA, rybB, rfaH, omrA and omrB genes.

4. The immunogenic composition of claim 3, further comprising an adjuvant.

5. The immunogenic composition of claim 3, wherein said mutated S. enterica serovar Typhimurium is attenuated or inactivated.

6. The immunogenic composition of claim 5, wherein said inactivated S. enterica serovar Typhimurium is a bacterial ghost.

7. A method of inducing an immune response in an animal to S. enterica comprising administering to said animal an immunologically effective amount of the immunogenic composition of claim 3.

8. The method of claim 7, wherein said immunogenic composition further comprises an adjuvant.

9. The method of claim 7, wherein said novel, mutated S. enterica serovar Typhimurium in said immunogenic composition is attenuated or inactivated.

10. A method of reducing an animal's carriage of S. enterica comprising administering to said animal an immunologically effective amount of the immunogenic composition of claim 3, wherein said immunologically effective amount of said immunogenic composition generates an immune response in said animal that reduces said S. enterica carriage.

11. The method of claim 10, wherein said immunogenic composition further comprises an adjuvant.

12. The method of claim 10, wherein said mutated S. enterica serovar Typhimurium in said immunogenic composition is attenuated or inactivated.

13. A method of reducing S. enterica colonization of an animal comprising administering to said animal an immunologically effective amount of the immunogenic composition of claim 3, wherein said immunologically effect amount of said immunogenic composition generates an immune response in said animal which reduces said S. enterica colonization.

14. The method of claim 13, wherein said immunogenic composition further comprises an adjuvant.

15. The method of claim 13, wherein said mutated S. enterica serovar Typhimurium in said immunogenic composition is attenuated or inactivated.

16. A kit comprising a first container comprising a mutated S. enterica serovar Typhimurium; a second container comprising a pharmaceutically acceptable carrier or diluent; written instructions for use; and optionally a third container comprising an adjuvant, wherein said mutated S. enterica serovar Typhimurium comprises a null mutation in invR, micA, rybB, rfaH, omrA and omrB genes.

17. The kit of claim 16, wherein said mutated S. enterica serovar Typhimurium is attenuated or inactivated.

18. The kit of claim 16, wherein said mutated S. enterica serovar Typhimurium is selected from the group consisting of S. enterica serovar Typhimurium strain BBS 866 deposited under the accession NRRL B-50989, S. enterica serovar Typhimurium strain BBS 1134 deposited under the accession NRRL B-50990, and a combination thereof.

19. The immunogenic composition of claim 3, wherein said mutated S. enterica serovar Typhimurium selected from the group consisting of S. enterica serovar Typhimurium strain BBS 866 deposited under the accession NRRL B-50989, S. enterica serovar Typhimurium strain BBS 1134 deposited under the accession NRRL B-50990, and a combination thereof.

20. An immunogenic composition comprising a pharmaceutically acceptable carrier or diluent and a membrane fraction of a mutated *S. enterica* serovar Typhimurium comprising a null mutation in invR, micA, rybB, rfaH, omrA and omrB genes.

21. The method of claim 7, wherein the immune response that is induced is cross-reactive with *S. enterica* serovar Typhimurium, *S. enterica* serovar Choleraesuis, and *S. enterica* serovar Heidelberg.

22. The method of claim 10, wherein said *S. enterica* carriage is due to *S. enterica* serovar Typhimurium, *S. enterica* serovar Choleraesuis, or *S. enterica* serovar Heidelberg.

23. The method of claim 13, wherein the generated immune response is cross-reactive with *S. enterica* serovar Typhimurium, *S. enterica* serovar Choleraesuis, and *S. enterica* serovar Heidelberg.

* * * * *

UNITED STATES PATENT AND TRADEMARK OFFICE
CERTIFICATE OF CORRECTION

PATENT NO. : 9,868,769 B2
APPLICATION NO. : 15/108725
DATED : January 16, 2018
INVENTOR(S) : Bradley L. Bearson and Shawn M. Bearson Page 1 of 1

It is certified that error appears in the above-identified patent and that said Letters Patent is hereby corrected as shown below:

On the Title Page

Item (54) and in the Specification, Column 1, change "MUTATED SALMONELLA ENTERIACA" to "MUTATED SALMONELLA ENTERICA"

Signed and Sealed this
Twenty-ninth Day of May, 2018

Andrei Iancu
*Director of the United States Patent and Trademark Office*